United States Patent
Fischer et al.

(10) Patent No.: US 7,718,186 B2
(45) Date of Patent: May 18, 2010

(54) 2-ALKOXY-6-ALKYLPHENYL-SUBSTITUTED SPIROCYCLIC TETRAMIC ACID DERIVATIVES

(75) Inventors: Reiner Fischer, Monheim (DE); Stefan Lehr, Liederbach (DE); Mark Wilhelm Drewes, Langenfeld (DE); Dieter Feucht, Eschborn (DE); Olga Malsam, Rösrath (DE); Guido Bojack, Wiesbaden (DE); Christian Arnold, Langenfeld (DE); Thomas Auler, Leichlingen (DE); Martin Jeffrey Hills, Idstein (DE); Heinz Kehne, Hofheim (DE); Chris Rosinger, Hofheim (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 11/666,988

(22) PCT Filed: Oct. 21, 2005

(86) PCT No.: PCT/EP2005/011342

§ 371 (c)(1),
(2), (4) Date: Nov. 28, 2007

(87) PCT Pub. No.: WO2006/056281

PCT Pub. Date: Jun. 1, 2006

(65) Prior Publication Data

US 2008/0220973 A1    Sep. 11, 2008

(30) Foreign Application Priority Data

Nov. 4, 2004    (DE)    .......... 10 2004 053 192

(51) Int. Cl.
*A01N 43/36*  (2006.01)
*C07D 207/46* (2006.01)
*C07D 491/10* (2006.01)
*A01P 13/00*  (2006.01)

(52) U.S. Cl. .......... 424/405; 504/283; 514/425; 548/544

(58) Field of Classification Search .......... 548/544; 514/425; 504/283
See application file for complete search history.

(56) References Cited

U.S. PATENT DOCUMENTS

| | | |
|---|---|---|
| 4,021,224 A | 5/1977 | Pallos et al. |
| 4,186,130 A | 1/1980 | Teach |
| 4,623,727 A | 11/1986 | Hubele |
| 4,639,266 A | 1/1987 | Heubach et al. |
| 4,881,966 A | 11/1989 | Nyffeler et al. |
| 4,891,057 A | 1/1990 | Sohn et al. |
| 4,902,340 A | 2/1990 | Hubele |
| 4,925,868 A | 5/1990 | Terao et al. |
| 4,985,063 A | 1/1991 | Fischer et al. |
| 5,045,560 A | 9/1991 | Fischer et al. |
| 5,116,836 A | 5/1992 | Fischer et al. |
| 5,225,434 A | 7/1993 | Bertram et al. |
| 5,258,527 A | 11/1993 | Krauskopf et al. |
| 5,314,863 A | 5/1994 | Löher et al. |
| 5,380,852 A | 1/1995 | Schütze et al. |
| 5,401,700 A | 3/1995 | Sohn et al. |
| 5,407,897 A | 4/1995 | Cary et al. |
| 5,462,913 A | 10/1995 | Fischer et al. |
| 5,504,057 A | 4/1996 | Fischer et al. |
| 5,516,750 A | 5/1996 | Willms et al. |
| 5,567,671 A | 10/1996 | Fischer et al. |
| 5,589,469 A | 12/1996 | Fischer et al. |
| 5,622,917 A | 4/1997 | Fischer et al. |
| 5,683,965 A | 11/1997 | Bachmann et al. |
| 5,700,758 A | 12/1997 | Rösch et al. |
| 5,811,374 A | 9/1998 | Bertram et al. |
| 5,830,826 A | 11/1998 | Fischer et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |

(Continued)

FOREIGN PATENT DOCUMENTS

CA    2 492 096 A1    1/2004

(Continued)

OTHER PUBLICATIONS

Bhattacharya, B., "Isoquinoline Derivatives: Part XVIII—Formation of 1-Alkyl-(or alkaryl or aryl)-3-methyl-7-chloro-(or 5-chloro)-isoquinolines," *Indian J. Chem.* 6:341-345, Council of Scientific and Industrial Research (1968).

(Continued)

*Primary Examiner*—David J Blanchard
*Assistant Examiner*—Kortney L Klinkel
(74) *Attorney, Agent, or Firm*—Sterne, Kessler, Goldstein & Fox P.L.L.C.

(57) ABSTRACT

The invention relates to novel 2-alkoxy-6-alkylphenyl-substituted spirocyclic tetramic acid derivatives of the formula (I)

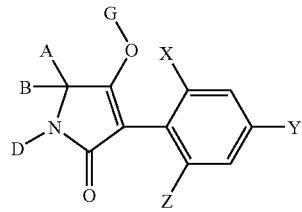

(I)

in which A, B, D, G, X, Y and Z are as defined above, to a plurality of processes and intermediates for their preparation and to their use as pesticides and/or herbicides, and also to selective herbicidal compositions comprising, firstly, the 2-alkoxy-6-alkylphenyl-substituted spirocyclic tetramic acid derivatives of the formula (I) and, secondly, at least one crop plant tolerance promoter compound.

15 Claims, No Drawings

U.S. PATENT DOCUMENTS

| | | |
|---|---|---|
| 6,251,827 B1 | 6/2001 | Ziemer et al. |
| 6,251,830 B1 | 6/2001 | Fischer et al. |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,511,942 B1 | 1/2003 | Lieb et al. |
| 6,589,976 B1 | 7/2003 | Fischer et al. |
| 6,608,211 B1 | 8/2003 | Hagemann et al. |
| 6,642,180 B1 | 11/2003 | Fischer et al. |
| 6,861,391 B1 | 3/2005 | Fischer et al. |
| 6,894,005 B1 | 5/2005 | Maetzke et al. |
| 2002/0072617 A1 | 6/2002 | Hagemann et al. |
| 2003/0171220 A1 | 9/2003 | Ziemer et al. |
| 2003/0216260 A1 | 11/2003 | Ruther et al. |
| 2004/0186328 A1 | 9/2004 | Perichon et al. |
| 2005/0054535 A1 | 3/2005 | Fischer et al. |
| 2006/0166829 A1 | 7/2006 | Fischer et al. |
| 2007/0015825 A1 | 1/2007 | Fischer et al. |
| 2007/0129252 A1 | 6/2007 | Fischer et al. |
| 2007/0244007 A1 | 10/2007 | Fischer et al. |
| 2007/0254949 A1 | 11/2007 | Bretschneider et al. |
| 2007/0265266 A1 | 11/2007 | Fischer et al. |
| 2007/0270416 A1 | 11/2007 | Funke et al. |
| 2007/0276023 A1 | 11/2007 | Fischer et al. |
| 2007/0298969 A1 | 12/2007 | Fischer et al. |
| 2008/0027114 A1 | 1/2008 | Funke et al. |
| 2008/0167188 A1 | 7/2008 | Fischer et al. |
| 2008/0188371 A1 | 8/2008 | Fischer et al. |
| 2008/0200499 A1 | 8/2008 | Fischer et al. |
| 2008/0287435 A1 | 11/2008 | Fischer et al. |
| 2008/0305955 A1 | 12/2008 | Bretschneider et al. |
| 2008/0318776 A1 | 12/2008 | Fischer et al. |
| 2009/0012100 A1 | 1/2009 | Fischer et al. |
| 2009/0012152 A1 | 1/2009 | Fischer et al. |
| 2009/0029858 A1 | 1/2009 | Fischer et al. |
| 2009/0215624 A1 | 8/2009 | Fischer et al. |
| 2009/0281157 A1 | 11/2009 | Fischer et al. |
| 2009/0298828 A1 | 12/2009 | Fischer et al. |

FOREIGN PATENT DOCUMENTS

| | | |
|---|---|---|
| CA | 2 497 074 A1 | 3/2004 |
| CA | 2 518 620 A1 | 9/2004 |
| CA | 2 544 537 A1 | 5/2005 |
| CA | 2 544 548 A1 | 5/2005 |
| CA | 2 546 815 A1 | 6/2005 |
| CA | 2 546 817 A1 | 6/2005 |
| CA | 2 552 737 A1 | 7/2005 |
| CA | 2 572 141 A1 | 1/2006 |
| GB | 2 266 888 A | 11/1993 |

OTHER PUBLICATIONS

Compagnon, P.L., and Miocque, M., "Addition des Réactifs Nucléophiles sur la Triple Liaison Nitrile," *Ann. Chim.* 5:11-22, Masson (1970).

Edward, J.T., and Jitrangsri, C., "Stereochemistry of the Bucherer-Bergs and Strecker Reactions of 4-*tert*-Butylcyclohexanone," *Can J. Chem.* 53:3339-3350, NRC Research Press (1975).

Harrison, H.R., et al., "Use of molecular sieves in the methyl esterification of carboxylic acids," *Chem. Ind.*, p. 1568, Society of Chemical Industry (1968).

Munday, L., "Amino-acids of the Cyclohexane Series. Part I.," *J. Chem. Soc.*, pp. 4372-4379, Royal Society of Chemistry (1961).

Schmierer, R., and Mildenberger, H., "Cyclisierung von N-Acylalanin-und N-Acylglycinestern," *Liebigs Ann. Chem.* 6:1095-1098, VCH Verlagsgesellschaft mbH (1985).

Sonntag, N.O.V., "The Reactions of Aliphatic Acid Chlorides," *Chem. Rev.* 52:237-416, American Chemical Society (1953).

Suzuki, S., et al., "Studies on antiviral agents. IV. Biological activity of tenuazonic acid derivatives," *Chem. Pharm. Bull.* 15:1120-1122, Pharmaceutical Society of Japan (1967).

Database CAPLUS on STN, Chemical Accession No. 1985:437721 English language abstract, Schmierer, R., and Mildenberger, H., "Cyclization of N-acylalanine and N-acylglycine esters," *Liebigs Ann. Chem.* 5:1095-1098, (1985) (Abstract for document NPL6).

Dialog File 351, Accession No. 4963457, Derwent WPI English language abstract for EP 0 346 620 A1 (listed as document FP1 on accompanying form PTO/SB/08A).

International Search Report for International Application No. PCT/EP2005/011342, European Patent Office, Netherlands, mailed on Jan. 4, 2006.

Co-pending U.S. Appl. No. 12/373,166, inventors Fischer, R., et al., filed Jul. 6, 2007.

Co-pending U.S. Appl. No. 12/304,904, inventors Fischer, R., et al., filed Jun. 5, 2007.

Co-pending U.S. Appl. No. 12/305,135, inventors Fischer, R., et al., filed Jun. 5, 2007.

Co-pending U.S. Appl. No. 12/304,958, inventors Fischer, R., et al., filed Jun. 5, 2007.

Co-pending U.S. Appl. No. 12/373,648, inventors Fischer, R., et al., filed Jul. 11, 2007.

Co-pending U.S. Appl. No. 12/373,205, inventors Fischer, R., et al., filed Jul. 6, 2007.

Co-pending U.S. Appl. No. 12/373,197, inventors Fischer, R., et al., filed Jul. 6, 2007.

Co-pending U.S. Appl. No. 12/373,188, inventors Fischer, R., et al., filed Jul. 6, 2007.

Office Action mailed Dec. 6, 1999, in U.S. Appl. No. 09/155,637, Lieb, V., et al., filed Sep. 29, 1998.

Office Action mailed May 15, 1998, in U.S. Appl. No. 08/875,872, Fischer R., et al., filed Aug. 5, 1997.

Office Action mailed Nov. 30, 1998, in U.S. Appl. No. 08/875,872, Fischer R., et al., filed Aug. 5, 1997.

Office Action mailed Jul. 21, 1999, in U.S. Appl. No. 08/875,872, Fischer R., et al., filed Aug. 5, 1997.

Office Action mailed Jan. 12, 2000, in U.S. Appl. No. 08/875,872, Fischer R., et al., filed Aug. 5, 1997.

Office Action mailed Feb. 6, 2001, in U.S. Appl. No. 08/875,872, Fischer R., et al., filed Aug. 5, 1997.

2-ALKOXY-6-ALKYLPHENYL-SUBSTITUTED SPIROCYCLIC TETRAMIC ACID DERIVATIVES

CROSS-REFERENCE TO RELATED APPLICATIONS

This is the U.S. National Stage of WO application number PCT/EP2005/011342, filed Oct. 21, 2005, now pending, which claims priority from DE 102004053192.7, filed Nov. 4, 2004, each of which is wholly incorporated by reference herein.

The invention relates to novel 2-alkoxy-6-alkylphenyl-substituted spirocyclic tetramic acid derivatives, to a plurality of processes and intermediates for their preparation and to their use as pesticides and/or herbicides. Moreover, the invention relates to novel selective herbicidal active compound combinations comprising, firstly, the 2-alkoxy-6-alkylphenyl-substituted spirocyclic tetramic acid derivatives and, secondly, a crop plant tolerance promoter compound, which combinations can be used with particularly good results for the selective control of weeds in various crops of useful plants.

3-Acylpyrrolidine-2,4-diones are described as having pharmaceutical properties (S. Suzuki et al. Chem. Pharm. Bull. 15 1120 (1967)). Furthermore, N-phenylpyrrolidine-2,4-diones were synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones); however, a herbicidal, insecticidal or acaricidal action of these compounds has hitherto not been described. Unsubstituted bicyclic 3-arylpyrrolidine-2,4-dione derivatives (EP-A-355 599 and EP-A-415 211) and substituted monocyclic 3-arylpyrrolidine-2,4-dione derivatives (EP-A-377 893 and EP-A-442 077) having herbicidal, insecticidal or acaricidal action are known.

Also known are polycyclic 3-arylpyrrolidine-4-dione derivatives (EP-A-442 073) and 1H-arylpyrrolidinedione derivatives (EP-A-456 063, EP-A-521 334, EP-A-596 298, EP-A-613 884, EP-A-613 885, WO 94/01 997, WO 95/26954, WO 95/20 572, EP-A-0 668 267, WO 96/25 395, WO 96 35 664, WO 97/01 535, WO 97/02 243, WO 97/36 868, WO 97/43275, WO/98/05638, WO 98/06721, WO 98/25928, WO 99/16748, WO 99/24437, WO 99/43649, WO 99/48869, WO 99/55673, WO 01/09092, WO 01/17972, WO 01/23354, WO 01/74770, WO 03/013249, WO 04/007448, WO 04/024688, WO 04/065336, WO 04/080962, WO 04/111042, WO 05/044791, WO 05/044796, WO 05/048710, WO 05/049569 and WO 05/066125).

However, in particular at low application rates and concentrations, the activity and the activity spectrum of these compounds are not always entirely satisfactory. Moreover, the compatibility with plants of these compounds is not always sufficient).

This invention now provides novel compounds of the formula (I)

(I)

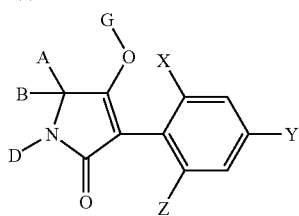

in which
X represents alkoxy,
Y represents alkyl and
Z represents $C_2$-$C_6$-alkyl,
A represents hydrogen, in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano-, or nitro-substituted aryl, arylalkyl or hetaryl,
B represents hydrogen, alkyl or alkoxyalkyl, or
A and B together with the carbon atom to which they are attached represent a saturated or unsaturated $C_4$-$C_8$-ring which optionally contains at least one heteroatom and which is optionally substituted by alkyl, alkoxy or haloalkyl,
D represents hydrogen or an optionally substituted radical from the group consisting of alkyl, alkenyl, alkynyl, alkoxyalkyl, alkylthioalkyl, saturated or unsaturated cycloalkyl in which optionally one or more ring members are replaced by heteroatoms, arylalkyl, aryl, hetarylalkyl or hetaryl, or
A and D together with the atoms to which they are attached represent a saturated or unsaturated unsubstituted or substituted cycle which is optionally interrupted by heteroatoms, and
G represents hydrogen (a) or represents one of the groups (b)

(c)

(d)

(e)

(f)

(g)

in which
E represents a metal ion equivalent or an ammonium ion,
L represents oxygen or sulfur,
M represents oxygen or sulfur,
$R^1$ represents in each case optionally substituted alkyl, alkenyl, alkoxyalkyl, alkylthioalkyl or polyalkoxyalkyl or represents in each case optionally halogen-, alkyl-, or alkoxy-substituted cycloalkyl or heterocyclyl or represents in each case optionally substituted phenyl, phenylalkyl, phenylalkenyl or hetaryl,
$R^2$ represents in each case optionally halogen-substituted alkyl, alkenyl, alkoxyalkyl or polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, R⁶ and R⁷ independently of one another represent hydrogen, represent in each case optionally halogen-substituted alkyl, cycloalkyl, alkenyl, alkoxy, alkoxyalkyl, represent in each case optionally substituted phenyl or benzyl, or together with the N-atom to which they are attached form an optionally substituted cycle which optionally contains oxygen or sulfur.

Depending inter alia on the nature of the substituents, the compounds of the formula (I) may be present as geometrical and/or optical isomers or isomer mixtures of varying composition which, if desired, can be separated in a customary manner. The present invention provides both the pure isomers and the isomer mixtures, their preparation and use and compositions comprising them. However, for the sake of simplicity, hereinbelow only compounds of the formula (I) are referred to, although what is meant are both the pure compounds, and if appropriate, mixtures having varying proportions of isomeric compounds.

Including the different meanings (a), (b), (c), (d), (e), (f) and (g) of group G, the following principal structures (I-a) to (I-g) result:

(I-a):

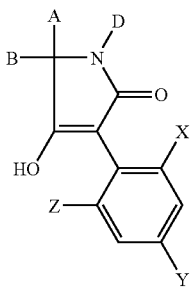

(I-b):

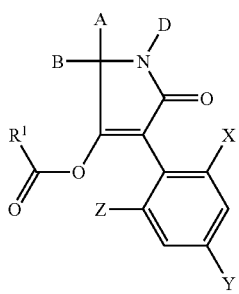

(I-c):

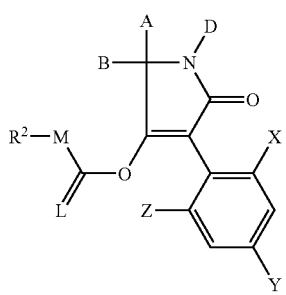

(I-d):

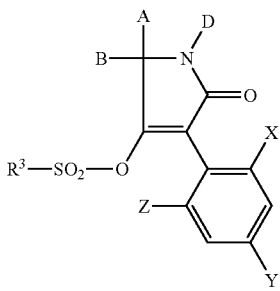

(I-e):

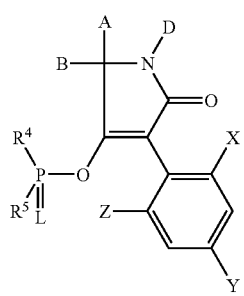

(I-f):

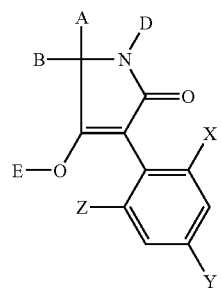

(I-g):

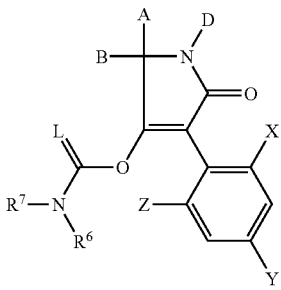

in which

A, B, D, E, L, M, X, Y, Z, R¹, R², R³, R⁴, R⁵, R⁶ and R⁷ are as defined above.

Furthermore, it has been found that the novel compounds of the formula (I) are obtained by one of the processes described below:

(A) Compounds of the formula (I-a),

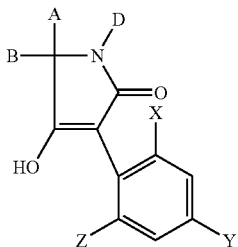
(I-a)

in which
A, B, D, X, Y and Z are as defined above,
are obtained when
compounds of the formula (II),

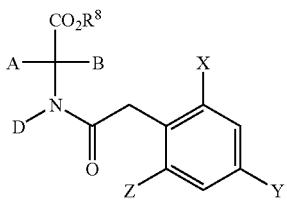
(II)

in which
A, B, D, X, Y and Z are as defined above,
and
$R^8$ represents alkyl (preferably $C_1$-$C_6$-alkyl)
are condensed intramolecularly in the presence of a diluent and in the presence of a base.

(B) Compounds of the formula (I-b) shown above in which A, B, D, $R^1$, X, Y and Z are as defined above are obtained when compounds of the formula (I-a) shown above in which A, B, D, X, Y and Z are as defined above are reacted α) with acid halides of the formula (III),

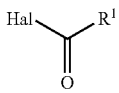
(III)

in which
$R^1$ is as defined above and
Hal represents halogen (in particular chlorine or bromine)
or β) with carboxylic anhydrides of the formula (IV),

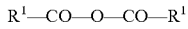 $R^1$—CO—O—CO—$R^1$ (IV)

in which
$R^1$ is as defined above,
if appropriate in the presence of a diluent and if appropriate in the presence of an acid binder.

(C) Compounds of the formula (I-c) shown above in which A, B, D, $R^2$, M, X, Y and Z are as defined above and L represents oxygen are obtained when compounds of the formula (I-a) shown above in which A, B, D, X, Y and Z are as defined above are in each case reacted
with chloroformic esters or chloroformic thioesters of the formula (V),

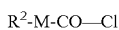 $R^2$-M-CO—Cl (V)

in which
$R^2$ and M are as defined above,
if appropriate in the presence of a diluent and if appropriate in the presence of an acid binder.

(D) Compounds of the formula (I-c) shown above in which A, B, D, $R^2$, M, X, Y and Z are as defined above and L represents sulfur are obtained when compounds of the formula (I-a) shown above in which A, B, D, X, Y and Z are as defined above are in each case α) reacted with chloromonothioformic esters or chlorodithioformic esters of the formula (VI),

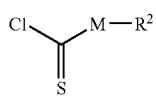
(VI)

in which
M and $R^2$ are as defined above,
if appropriate in the presence of a diluent and if appropriate in the presence of an acid binder,
or β) reacted with carbon disulfide and then with compounds of the formula (VII),

 $R^2$-Hal (VII)

in which
$R^2$ is as defined above and
Hal represents chlorine, bromine or iodine,
if appropriate in the presence of a diluent and if appropriate in the presence of a base.

(E) Compounds of the formula (I-d) shown above in which A, B, D, $R^3$, X, Y and Z are as defined above are obtained when compounds of the formula (I-a) shown above in which A, B, D, X, Y and Z are as defined above are in each case reacted
with sulfonyl chlorides of the formula (VIII),

 $R^3$—$SO_2$—Cl (VIII)

in which
$R^3$ is as defined above,
if appropriate in the presence of a diluent and if appropriate in the presence of an acid binder.

(F) Compounds of the formula (I-e) shown above in which A, B, D, L, $R^4$, $R^5$, X, Y and Z are as defined above are obtained when compounds of the formula (I-a) shown above in which A, B, D, X, Y and Z are as defined above are in each case reacted
with phosphorus compounds of the formula (IX),

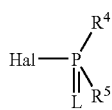
(IX)

in which
L, $R^4$ and $R^5$ are as defined above and
Hal represents halogen (in particular chlorine or bromine),
if appropriate in the presence of a diluent and if appropriate in the presence of an acid binder.

(G) Compounds of the formula (I-f) shown above in which A, B, D, E, X, Y and Z are as defined above are obtained when compounds of the formula (I-a) shown above in which A, B, X, Y and Z are as defined above are in each case reacted
with metal compounds or amines of the formula (X) or (XI),

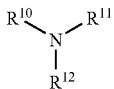

(X) Me(OR$^{10}$)$_t$ (XI)

in which
Me represents a mono- or divalent metal (preferably an alkali metal or alkaline earth metal, such as lithium, sodium, potassium, magnesium or calcium),
t represents the number 1 or 2 and
R$^{10}$, R$^{11}$, R$^{12}$ independently of one another represent hydrogen or alkyl (preferably C$_1$-C$_8$-alkyl),
if appropriate in the presence of a diluent.
(H) Compounds of the formula (I-g) shown above in which A, B, D, L, R$^6$, R$^7$, X, Y and Z are as defined above are obtained when compounds of the formula (I-a) shown above in which A, B, D, X, Y and Z are as defined above are in each case
α) reacted with isocyanates or isothiocyanates of the formula (XII),

R$^6$—N=C=L  (XII)

in which
R$^6$ and L are as defined above,
if appropriate in the presence of a diluent and if appropriate in the presence of a catalyst, or
β) reacted with carbamoyl chlorides or thiocarbamoyl chlorides of the formula (XIII),

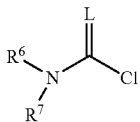

(XIII)

in which
L, R$^6$ and R$^7$ are as defined above,
if appropriate in the presence of a diluent and if appropriate in the presence of an acid binder.
(I) Furthermore, it has been found that compounds of the formula (I-a) shown above in which A, B, D, X, Y and Z are as defined above are obtained when compounds of the formula (I-a')

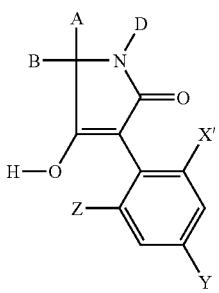

(I-a')

in which
A, B, D, Y and Z are as defined above, and
X' represents chlorine, bromine, iodine, preferably bromine,
are reacted with alcohols of the formula (XXV)

Alk-OH  (XXV)

in which
Alk represents alkyl and
in the presence of a solvent, a base and a catalyst, suitable catalysts being in particular copper(I) salts.

Furthermore, it has been found that the novel compounds of the formula (I) are highly active pesticides, preferably insecticides and/or acaricides and/or herbicides.

Surprisingly, it has also been found that certain substituted cyclic ketoenols, when used together with crop plant tolerance promoter compounds (safeners/antidotes) described below, are highly suitable for preventing damage to the crop plant and can be used particularly advantageously as broad-spectrum effective combination preparations for the selective control of unwanted plants in crops of useful plants, such as, for example, in cereals, but also maize, soybeans and rice.

The invention also provides selective herbicidal compositions comprising an effective amount of a combination of active compounds comprising, as components,
(a') at least one substituted tetramic acid derivative of the formula (I) in which A, B, D, G, X, Y and Z are as defined above and (b') at least one crop plant tolerance promoter compound from the following group of compounds:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxy-acetate (cloquintocet-mexyl—cf. also related compounds in EP-A-86750, EP-A-94349, EP-A-191736, EP-A492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N, N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloro-acetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloro-quinoline-8-oxyacetate, 1-allyloxyprop-2-yl 5-chloroquinoline-8-oxyacetate, methyl 5-chloro-quinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxy-malonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxy-benzophenone, 1-bromo-4-chloromethylsulfonylbenzene, 1-[4-(N-2-methoxybenzoylsulfamoyl)-phenyl]-3-methylurea (also known as N-(2-methoxybenzoyl)-4-[(methylaminocarbonyl)-amino]benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclopropylaminocarbonyl)benzene-sulfonamide, and/or one of the following compounds, defined by general formulae, of the general formula (IIa)

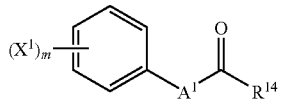
(IIa)

or of the general formula (IIb)

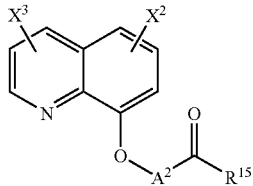
(IIb)

or of the formula (IIc)

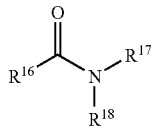
(IIc)

where m represents a number 0, 1, 2, 3, 4 or 5, $A^1$ represents one of the divalent heterocyclic groupings shown below

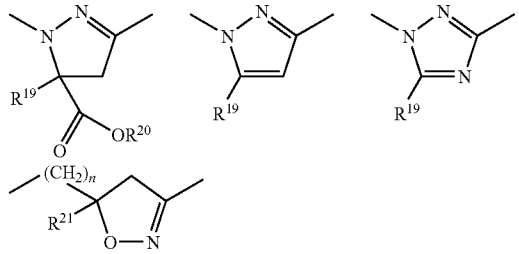

n represents a number 1, 2, 3, 4 or 5, $A^2$ represents optionally $C_1$-$C_4$-alkyl- and/or $C_1$-$C_4$-alkoxy-carbonyl- and/or $C_1$-$C_4$-alkenyloxy-carbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)-amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di-($C_1$-$C_4$-alkyl)-amino, $R^{16}$ represents in each case optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

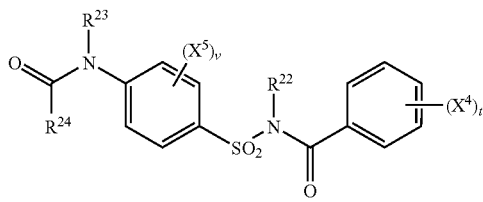
(IId)

or of the general formula (IIe)

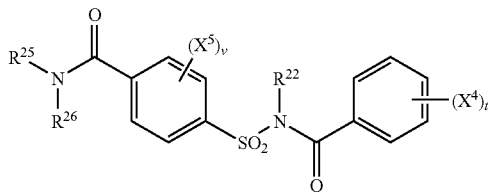
(IIe)

where
t represents a number between 0 and 5,
v represents a number between 0 and 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl,
$X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and
$X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae given above and below are illustrated below:
X preferably represents $C_1$-$C_4$-alkoxy,
Y preferably represents $C_1$-$C_3$-alkyl,
Z preferably represents ethyl, n-propyl or n-butyl,
A preferably represents hydrogen or optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulfur or represents in each case optionally halogen-, $C_1$-$C_6$-alkyl, $C_1$-$C_6$-haloalkyl, $C_1$-$C_6$-alkoxy, $C_1$-$C_6$-haloalkoxy-, cyano- or nitro-substituted phenyl, naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl,
B preferably represents hydrogen, $C_1$-$C_{12}$-alkyl or $C_1$-$C_8$-alkoxy-$C_1$-$C_6$-alkyl, or
A, B and the carbon atom to which they are attached preferably represent saturated $C_4$-$C_8$-cycloalkyl in which optionally one methylene group is replaced by oxygen or sulfur and which is optionally substituted by $C_1$-$C_6$-alkyl, $C_1$-$C_4$-haloalkyl or $C_1$-$C_6$-alkoxy,
D preferably represents hydrogen, represents $C_1$-$C_8$-alkyl, $C_1$-$C_8$-alkenyl, $C_1$-$C_6$-alkoxy-$C_2$-$C_4$-alkyl or $C_1$-$C_6$-alkylthio-$C_2$-$C_4$-alkyl, each of which is optionally mono- to trisubstituted by halogen, represents $C_3$-$C_8$-cycloalkyl which is optionally mono- to trisubstituted by halogen, $C_1$-$C_4$-alkyl, $C_1$-$C_4$-alkoxy or $C_1$-$C_2$-haloalkyl,
A and D together preferably represent a $C_3$-$C_8$-alkanediyl or $C_3$-$C_6$-alkenediyl group in which in each case optionally by one methylene group is replaced by oxygen or sulfur and which are in each case optionally mono- to disubstituted by halogen, hydroxyl, $C_1$-$C_4$-alkyl or $C_1$-$C_4$-alkoxy, or by a further $C_3$-$C_6$-alkanediyl, $C_3$-$C_6$-alkenediyl or $C_4$-$C_6$-alkanedienediyl group which forms a fused-on ring,
G preferably represents hydrogen (a) or represents one of the groups

(b)

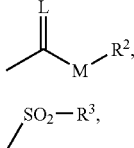
(c)

(d)

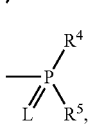
(e)

E or
(f)

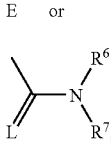
(g)

in which
E represents a metal ion equivalent or an ammonium ion,
L represents oxygen or sulfur and
M represents oxygen or sulfur,
$R^1$ preferably represents $C_1$-$C_{20}$-alkyl, $C_2$-$C_{20}$-alkenyl, $C_1$-$C_6$-alkoxy-$C_1$-$C_6$-alkyl, $C_1$-$C_6$-alkylthio-$C_1$-$C_6$-alkyl or poly-$C_1$-$C_4$-alkoxy-$C_1$-$C_4$-alkyl, each of which is optionally mono- to hepta-substituted by halogen, mono- to disubstituted by cyano, monosubstituted by $COR^{13}$, $C=N-OR^{13}$, $CO_2R^{13}$, or

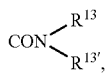

or represents $C_3$-$C_8$-cycloalkyl which is optionally mono- to trisubstituted by halogen, $C_1$-$C_4$-alkyl or $C_1$-$C_4$-alkoxy and in which optionally one or two not directly adjacent methylene groups are replaced by oxygen and/or sulfur, represents phenyl, phenyl-$C_1$-$C_2$-alkyl or phenyl-$C_1$-$C_2$-alkenyl, each of which is optionally mono- to trisubstituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio, $C_1$-$C_6$-alkylsulfinyl or $C_1$-$C_6$-alkylsulfonyl, represents 5- or 6-membered hetaryl which is optionally mono- to disubstituted by halogen or $C_1$-$C_6$-alkyl and which has one or two heteroatoms from the group consisting of oxygen, sulfur and nitrogen, $R^2$ preferably represents $C_1$-$C_{20}$-alkyl, $C_2$-$C_{20}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by halogen, represents $C_3$-$C_8$-cycloalkyl which is optionally mono- to disubstituted by halogen, $C_1$-$C_6$-alkyl or $C_1$-$C_6$-alkoxy or represents phenyl or benzyl, each of which is optionally mono- to trisubstituted by halogen, cyano, nitro, $C_1$-$C_6$-alkyl, $C_1$-$C_6$-alkoxy, $C_1$-$C_6$-haloalkyl or $C_1$-$C_6$-haloalkoxy, $R^3$ preferably represents $C_1$-$C_8$-alkyl which is optionally mono- to polysubstituted by halogen or represents phenyl or benzyl, each of which is optionally mono- to disubstituted by halogen, $C_1$-$C_6$-alkyl, $C_1$-$C_6$-alkoxy, $C_1$-$C_4$-haloalkyl, $C_1$-$C_4$-haloalkoxy, cyano or nitro, $R^4$ and $R^5$ independently of one another preferably represent $C_1$-$C_8$-alkyl, $C_1$-$C_8$-alkoxy, $C_1$-$C_8$-alkyl-amino, di-($C_1$-$C_8$-alkyl)amino, $C_1$-$C_8$-alkylthio or $C_2$-$C_8$-alkenylthio, each of which is optionally mono- to trisubstituted by halogen, or represent phenyl, phenoxy or phenylthio, each of which is optionally mono- to trisubstituted by halogen, nitro, cyano, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkyl or $C_1$-$C_4$-haloalkyl, $R^6$ and $R^7$ independently of one another preferably represent hydrogen, represent $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, each of which is optionally mono- to trisubstituted by halogen, represent phenyl or benzyl, each of which is optionally mono- to trisubstituted by halogen, $C_1$-$C_8$-alkyl, $C_1$-$C_8$-haloalkyl or $C_1$-$C_8$-alkoxy, or together represent a $C_3$-$C_6$-alkylene radical which is optionally mono- to disubstituted by $C_1$-$C_4$-alkyl and in which optionally one methylene group is replaced by oxygen or sulfur, $R^{13}$ preferably represents $C_1$-$C_6$-alkyl, $C_3$-$C_6$-alkenyl, $C_3$-$C_6$-alkynyl or $C_1$-$C_4$-alkoxy-$C_2$-$C_4$-alkyl, each of which is optionally mono- to trisubstituted by halogen, or represents $C_3$-$C_6$-cycloalkyl which is optionally mono- to disubstituted by halogen, $C_1$-$C_2$-alkyl or $C_1$-$C_2$-alkoxy and in which optionally one or two not directly adjacent methylene groups are replaced by oxygen or represents phenyl or phenyl-$C_1$-$C_2$-alkyl which are in each case optionally mono- to disubstituted by halogen, $C_1$-$C_4$-alkyl, $C_1$-$C_4$-alkoxy, $C_1$-$C_2$-haloalkyl, $C_1$-$C_2$-haloalkoxy, cyano or nitro, $R^{13'}$ preferably represents hydrogen, $C_1$-$C_6$-alkyl or $C_3$-$C_6$-alkenyl.

In the radical definitions mentioned as being preferred, halogen represents fluorine, chlorine, bromine and iodine, in particular fluorine, chlorine and bromine.

X particularly preferably represents methoxy, ethoxy, n-propoxy,

Y particularly preferably represents methyl or ethyl,

Z particularly preferably represents ethyl or n-propyl,

A particularly preferably represents hydrogen, $C_1$-$C_6$-alkyl, $C_1$-$C_2$-haloalkyl, $C_1$-$C_4$-alkoxy-$C_1$-$C_3$-alkyl or represents $C_3$-$C_6$-cycloalkyl which is optionally mono- to disubstituted by fluorine, chlorine, $C_1$-$C_2$-alkyl or $C_1$-$C_2$-alkoxy, B particularly preferably represents hydrogen, $C_1$-$C_2$-alkyl or $C_1$-$C_4$-alkoxy-$C_1$-$C_2$-alkyl, A, B and the carbon atom to which they are attached particularly preferably represent saturated $C_3$-$C_7$-cycloalkyl in which optionally one methylene group is replaced by oxygen and which is optionally monosubstituted by $C_1$-$C_4$-alkyl, $C_1$-$C_2$-haloalkyl or $C_1$-$C_4$-alkoxy, D particularly preferably represents hydrogen, D particularly preferably represents $C_1$-$C_6$-alkyl, $C_3$-$C_6$-alkenyl, $C_1$-$C_4$-alkoxy-$C_2$-$C_3$-alkyl or $C_1$-$C_4$-alkylthio-$C_2$-$C_3$-alkyl, each of which is optionally mono- to trisubstituted by fluorine or chlorine, represents $C_3$-$C_6$-cycloalkyl which is optionally mono- to disubstituted by fluorine, chlorine, $C_1$-$C_2$-alkyl, $C_1$-$C_2$-alkoxy or trifluoromethyl, with the proviso that in this case A only represents hydrogen or $C_1$-$C_3$-alkyl, A and D together particularly preferably represent a $C_3$-$C_5$-alkanediyl group in which optionally a methylene group is replaced by oxygen or sulfur and which is optionally mono- to disubstituted by $C_1$-$C_2$-alkyl or $C_1$-$C_2$-alkoxy, or A and D together with the atoms to which they are attached represent one of the groups AD-1 to AD-10 below

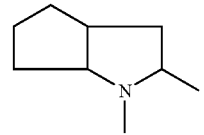

AD-1

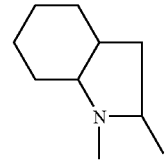

AD-2

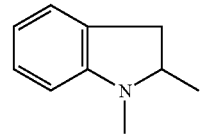

AD-3

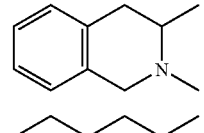

AD-4

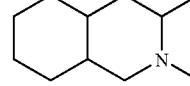

AD-5

-continued

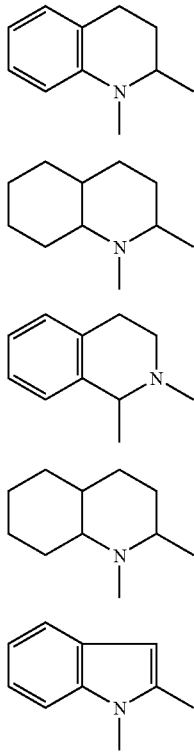

AD-6

AD-7

AD-8

AD-9

AD-10

G particularly preferably represents hydrogen (a) or represents one of the groups

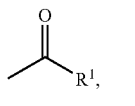 (b)

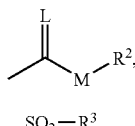 (c)

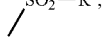 (d)

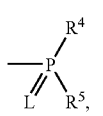 (e)

E or (f)

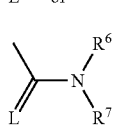 (g)

in which

E represents a metal ion equivalent or an ammonium ion,
L represents oxygen or sulfur and
M represents oxygen or sulfur,
$R^1$ particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl or poly-$C_1$-$C_3$-alkoxy-$C_1$-$C_2$-alkyl, each of which is optionally mono- to pentasubstituted by fluorine or chlorine, monosubstituted by cyano, monosubstituted by CO—$R^{13}$, C=N—$OR^{13}$ or $CO_2R^{13}$, or represents $C_3$-$C_6$-cycloalkyl which is optionally mono- to disubstituted by fluorine, chlorine, $C_1$-$C_2$-alkyl or $C_1$-$C_2$-alkoxy and in which optionally one or two not directly adjacent methylene groups are replaced by oxygen, represents phenyl or benzyl, each of which is optionally mono- to disubstituted by fluorine, chlorine, bromine, cyano, nitro, $C_1$-$C_4$-alkyl, $C_1$-$C_4$-alkylthio, $C_1$-$C_4$-alkylsulfinyl, $C_1$-$C_4$-alkylsulfonyl, $C_1$-$C_4$-alkoxy, $C_1$-$C_2$-haloalkyl or $C_1$-$C_2$-haloalkoxy, represents pyrazolyl, thiazolyl, pyridyl, pyrimidyl, furanyl or thienyl, each of which is optionally mono- to disubstituted by fluorine, chlorine, bromine or $C_1$-$C_2$-alkyl, $R^2$ particularly preferably represents $C_1$-$C_{10}$-alkyl, $C_2$-$C_{10}$-alkenyl, $C_1$-$C_4$-alkoxy-$C_2$-$C_4$-alkyl or poly-$C_1$-$C_4$-alkoxy-$C_2$-$C_4$-alkyl, each of which is optionally mono- to trisubstituted by fluorine or chlorine, represents $C_3$-$C_7$-cycloalkyl which is optionally monosubstituted by fluorine, chlorine, $C_1$-$C_2$-alkyl or $C_1$-$C_2$-alkoxy or represents phenyl or benzyl, each of which is optionally mono- to disubstituted by fluorine, chlorine, bromine, cyano, nitro, $C_1$-$C_4$-alkyl, methoxy, trifluoromethyl or trifluoromethoxy, $R^3$ particularly preferably represents $C_1$-$C_4$-alkyl which is optionally mono- to trisubstituted by fluorine or chlorine or represents phenyl or benzyl, each of which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- to disubstituted by fluorine, chlorine, bromine, nitro, cyano, $C_1$-$C_3$-alkoxy, trifluoromethoxy, $C_1$-$C_3$-alkylthio, $C_1$-$C_3$-alkyl or trifluoromethyl, $R^6$ and $R^7$ independently of one another particularly preferably represent hydrogen, represent $C_1$-$C_6$-alkyl, $C_3$-$C_6$-cycloalkyl, $C_1$-$C_4$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl which is optionally mono- to disubstituted by fluorine, chlorine, bromine, trifluoromethyl, $C_1$-$C_4$-alkyl or $C_1$-$C_4$-alkoxy, or together represent a $C_5$-$C_6$-alkylene radical which is optionally mono- to disubstituted by methyl and in which optionally one methylene group is replaced by oxygen, $R^{13}$ particularly preferably represents $C_1$-$C_4$-alkyl, $C_3$-$C_4$-alkenyl, $C_3$-$C_4$-alkynyl or $C_1$-$C_4$-alkoxy-$C_2$-$C_3$-alkyl or $C_3$-$C_4$-cycloalkyl in which optionally one methylene group is replaced by oxygen.

In the radical definitions mentioned as being particularly preferred, halogen represents fluorine, chlorine and bromine, in particular fluorine and chlorine.

X very particularly preferably represents methoxy or ethoxy,
Y very particularly preferably represents methyl,
Z very particularly preferably represents ethyl,
A very particularly preferably represents hydrogen, methyl, ethyl, n-propyl, isopropyl, n-butyl, isobutyl, sec-butyl, tert-butyl, trifluoromethyl, cyclopropyl, cyclopentyl or cyclohexyl,
B very particularly preferably represents hydrogen, methyl or ethyl, or A, B and the carbon atom to which they are attached very particularly preferably represent saturated $C_6$-cycloalkyl in which optionally one methylene group is replaced by oxygen and which is optionally monosubstituted by methyl, trifluoromethyl, methoxy, ethoxy, n-propoxy, isopropoxy, n-butoxy or isobutoxy, D very particularly preferably represents hydrogen, D also very particularly preferably represents methyl, ethyl, n-propyl, isopropyl, n-butyl, sec-butyl, isobutyl, cyclopropyl, cyclopentyl or cyclohexyl, with the proviso that in this case A only represents hydrogen, methyl or ethyl, A and D together very particularly preferably represent a $C_3$-$C_4$-alkanediyl group in which in each case optionally one methylene group is replaced by oxygen or sulfur and which is optionally mono- to disubstituted by methyl or methoxy or A and D together with the atoms to which they are attached represent the following group:

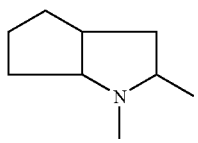

AD-1

G very particularly preferably represents hydrogen (a) or represents one of the groups

(b)

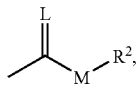

(c)

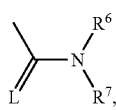

(g)

in which

E represents a metal ion equivalent or an ammonium ion,

L represents oxygen and

M represents oxygen or sulfur, $R^1$ very particularly preferably represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl or poly-$C_1$-$C_2$-alkoxy-$C_1$-$C_2$-alkyl, each of which is optionally mono- to trisubstituted by fluorine or chlorine, or represents cyclopropyl, cyclopentyl or cyclohexyl, each of which is optionally monosubstituted by fluorine, chlorine, methyl, ethyl or methoxy, represents phenyl which is optionally monosubstituted by fluorine, chlorine, bromine, cyano, nitro, methyl, ethyl, n-propyl, isopropyl, methoxy, ethoxy, methylthio, ethylthio, methyl-sulfinyl, ethylsulfinyl, methylsulfonyl, ethylsulfonyl, trifluoromethyl or trifluoromethoxy, represents furanyl, thienyl or pyridyl, each of which is optionally monosubstituted by chlorine, bromine or methyl, $R^2$ very particularly preferably represents $C_1$-$C_8$-alkyl, $C_2$-$C_6$-alkenyl or $C_1$-$C_3$-alkoxy-$C_2$-$C_3$-alkyl, cyclopentyl or cyclohexyl, or represents phenyl or benzyl, each of which is optionally monosubstituted by fluorine, chlorine, bromine, cyano, nitro, methyl, methoxy, trifluoromethyl or trifluoromethoxy, $R^6$ very particularly preferably represents hydrogen, represents $C_1$-$C_4$-alkyl, $C_3$-$C_6$-cycloalkyl or allyl, represents phenyl which is optionally monosubstituted by fluorine, chlorine, bromine, methyl, methoxy or trifluoromethyl, $R^7$ very particularly preferably represents methyl, ethyl, n-propyl, isopropyl or allyl, $R^6$ and $R^7$ together very particularly preferably represent a $C_5$-$C_6$-alkylene radical in which optionally one methylene group is replaced by oxygen.

X especially represents methoxy or ethoxy,

Y especially represents methyl,

Z especially represents ethyl,

A especially represents methyl, ethyl or cyclopropyl,

B especially represents hydrogen or methyl, or

A, B and the carbon atom to which they are attached especially represent saturated $C_6$-cycloalkyl which is optionally monosubstituted by methyl, ethoxy or n-butoxy, D especially represents hydrogen, D also especially represents methyl, with the proviso that in this case A only represents ethyl, A and D together especially represent a $C_3$-$C_4$-alkanediyl group which is optionally monosubstituted by methoxy, G especially represents hydrogen (a) or represents one of the groups (b)

(c)

in which $R^1$ especially represents $C_1$-$C_6$-alkyl or $C_1$-$C_2$-alkoxy-$C_1$-$C_2$-alkyl, $R^2$ especially represents $C_1$-$C_8$-alkyl.

The general or preferred radical definitions or illustrations given above can be combined with one another as desired, i.e. including combinations between the respective ranges and preferred ranges. They apply to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Especially preferred according to the invention are the compounds of the formula (I) which contain a combination of the meanings listed above as being especially preferred.

Saturated or unsaturated hydrocarbon radicals, such as alkyl, alkanediyl or alkenyl, can in each case be straight-chain or branched as far as this is possible, including in combination with heteroatoms, such as, for example, an alkoxy.

Optionally substituted radicals can be mono- or polysubstituted, where in the case of polysubstitution the substituents can be identical or different.

In addition to the compounds mentioned in the Preparation Examples, the following compounds of the formula (I-a) may be specifically mentioned:

TABLE 1

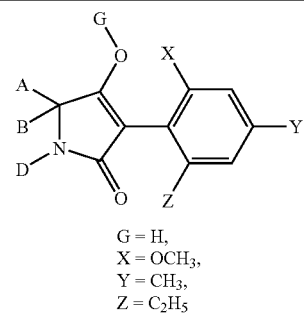

G = H,
X = OCH$_3$,
Y = CH$_3$,
Z = C$_2$H$_5$

| A | B | D |
|---|---|---|
| CH$_3$ | H | H |
| C$_2$H$_5$ | H | H |
| C$_3$H$_7$ | H | H |
| i-C$_3$H$_7$ | H | H |
| C$_4$H$_9$ | H | H |
| i-C$_4$H$_9$ | H | H |
| s-C$_4$H$_9$ | H | H |
| t-C$_4$H$_9$ | H | H |
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| C$_4$H$_9$ | CH$_3$ | H |
| i-C$_4$H$_9$ | CH$_3$ | H |
| s-C$_4$H$_9$ | CH$_3$ | H |
| t-C$_4$H$_9$ | CH$_3$ | H |
| C$_2$H$_5$ | C$_2$H$_5$ | H |
| C$_3$H$_7$ | C$_3$H$_7$ | H |
| cyclopropyl | CH$_3$ | H |
| cyclopentyl | CH$_3$ | H |
| cyclohexyl | CH$_3$ | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CHi-C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHO-i-C$_3$H$_7$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |
| —CH$_2$—CH—(CH$_2$)$_2$—CH— with bridging CH$_2$ | | H |

TABLE 1-continued

| A | D | B |
|---|---|---|
| —CH$_2$—CH—CH—CH$_2$— with (CH$_2$)$_4$ bridge | | H |
| —CH$_2$—CH—CH—(CH$_2$)$_2$— with (CH$_2$)$_3$ bridge | | H |
| indanyl | | H |
| tetrahydronaphthyl | | H |
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CHCH$_3$— | | H |
| —CH$_2$—CH(OCH$_3$)—CH$_2$— | | H |
| —CH$_2$—CH=CH—CH$_2$— | | H |
| —CH$_2$—CH—CH—CH$_2$— with O bridge (epoxide) | | H |
| —CH$_2$—S—CH$_2$— | | H |
| —CH$_2$—S—(CH$_2$)$_2$— | | H |
| —(CH$_2$)$_2$—S—CH$_2$— | | H |
| —CH$_2$—CH—CH— with (CH$_2$)$_3$ bridge | | H |
| H | CH$_3$ | H |
| H | C$_2$H$_5$ | H |
| H | C$_3$H$_7$ | H |
| H | i-C$_3$H$_7$ | H |
| H | cyclopropyl | H |
| H | cyclopentyl | H |
| H | cyclohexyl | H |
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ | cyclopropyl | H |
| CH$_3$ | cyclopentyl | H |
| CH$_3$ | cyclohexyl | H |

TABLE 1-continued

| | | |
|---|---|---|
| —CH$_2$—CH———CH—<br>        |            |<br>      CH$_2$—O—CH$_2$ | | H |
| C$_2$H$_5$ | CH$_3$ | H |
| C$_2$H$_5$ | C$_2$H$_5$ | H |

A, B, D, X, Y and Z as stated in Table 1
Table 2 G=CH$_3$—CO
Table 3 G=C$_2$H$_5$—CO
Table 4 G=C$_3$H$_7$—CO
Table 5 G=i-C$_3$H$_7$—CO
Table 6 G=C$_4$H$_9$—CO
Table 7 G=i-C$_4$H$_9$—CO
Table 8 G=s-C$_4$H$_9$—CO
Table 9 G=t-C$_4$H$_9$—CO G = 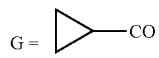

Table 11 G=H$_3$C—O—CH$_2$—CO
Table 12 G=H$_5$C$_2$—O—CH$_2$—CO
Table 13 G=H$_3$C—S—CH$_2$—CO
Table 14 G=H$_5$C$_2$—S—CH$_2$—CO
Table 15 G=CH$_3$—O—CO
Table 16 G=C$_2$H$_5$—O—CO
Table 17 G=C$_3$H$_7$—O—CO
Table 18 G=i-C$_3$H$_7$—O—CO
Table 19 G=C$_4$H$_9$—O—CO
Table 20 G=i-C$_4$H$_9$—O—CO
Table 21 G=s-C$_4$H$_9$—O—CO
Table 22 G=t-C$_4$H$_9$—O—CO
Table 23 G=t-C$_4$H$_9$—CH$_2$—O—CO
Table 24 G=C$_6$H$_5$—CH$_2$—O—CO
Table 25 G=C$_6$H$_5$—O—CO
Table 26 G=CH$_3$—S—CO
Table 27 G=C$_2$H$_5$—S—CO
Table 28 G=C$_3$H$_7$—S—CO
Table 29 G=i-C$_3$H$_7$—S—CO
Table 30 G=C$_4$H$_9$—S—CO
Table 31 G=i-C$_4$H$_9$—S—CO
Table 32 G=s-C$_4$H$_9$—S—CO
Table 33 G=t-C$_4$H$_9$—S—CO
Table 34 G=t-C$_4$H$_9$—CH$_2$—S—CO
Table 35 G=C$_6$H$_5$—CH$_2$—S—CO
Table 36 A, B and D as stated in Table 1 and G=H, X=OC$_2$H$_5$; Y=CH$_3$; Z=C$_2$H$_5$.

A, B and D as stated in Table 1 and X, Y and Z as stated in Table 36
Table 37 G=CH$_3$—CO
Table 38 G=C$_2$H$_5$—CO
Table 39 G=C$_3$H$_7$—CO
Table 40 G=i-C$_3$H$_7$—CO
Table 41 G=C$_4$H$_9$—CO
Table 42 G=i-C$_4$H$_9$—CO
Table 43 G=s-C$_4$H$_9$—CO
Table 44 G=t-C$_4$H$_9$—CO G = 

Table 46 G=H$_3$C—O—CH$_2$—CO
Table 47 G=H$_5$C$_2$—O—CH$_2$—CO
Table 48 G=H$_3$C—S—CH$_2$—CO
Table 49 G=H$_5$C$_2$—S—CH$_2$—CO
Table 50 G=CH$_3$—O—CO
Table 51 G=C$_2$H$_5$—O—CO
Table 52 G=C$_3$H$_7$—O—CO
Table 53 G=i-C$_3$H$_7$—O—CO
Table 54 G=C$_4$H$_9$—O—CO
Table 55 G=i-C$_4$H$_9$—O—CO
Table 56 G=s-C$_4$H$_9$—O—CO
Table 57 G=t-C$_4$H$_9$—O—CO
Table 58 G=t-C$_4$H$_9$—CH$_2$—O—CO
Table 59 G=C$_6$H$_5$—CH$_2$—O—CO
Table 60 G=C$_6$H$_5$—O—CO
Table 61 G=CH$_3$—S—CO
Table 62 G=C$_2$H$_5$—S—CO
Table 63 G=C$_3$H$_7$—S—CO
Table 64 G=i-C$_3$H$_7$—S—CO
Table 65 G=C$_4$H$_9$—S—CO
Table 66 G=i-C$_4$H$_9$—S—CO
Table 67 G=s-C$_4$H$_9$—S—CO
Table 68 G=t-C$_4$H$_9$—S—CO
Table 69 G=t-C$_4$H$_9$—CH$_2$—S—CO
Table 70 G=C$_6$H$_5$—CH$_2$—S—CO Preferred definitions of the groups listed above in connection with the crop plant tolerance promoter compounds ("herbicide safeners") of the formulae (IIa), (IIb), (IIc), (IId) and (IIe) are defined below.

m preferably represents the numbers 0, 1, 2, 3 or 4.

$A^1$ preferably represents one of the divalent heterocyclic groupings shown below

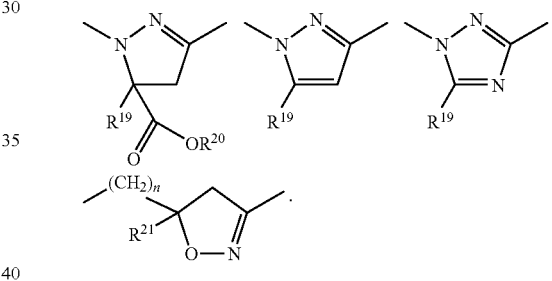

n preferably represents the numbers 0, 1, 2, 3 or 4.

$A^2$ preferably represents in each case optionally methyl-, ethyl-, methoxycarbonyl- or ethoxycarbonyl- or allyloxycarbonyl-substituted methylene or ethylene.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents in each case optionally fluorine-, chlorine-, and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl.

$R^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl, or together with $R^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

$R^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

v preferably represents the numbers 0, 1, 2, 3 or 4.

t preferably represents the numbers 0, 1, 2, 3 or 4.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclo-pentyl, cyclohexyl, cyclopropyloxy, cyclobutyloxy, cyclopentyloxy, cyclohexyloxy, cyclo-propylthio, cyclobutylthio, cyclopentylthio, cyclohexylthio, cyclopropylamino, cyclobutyl-amino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

| Example No. | (Positions) $(X^1)_m$ | $A^1$ | $R^{14}$ |
|---|---|---|---|
| IIa-1 | (2) Cl, (4) Cl | | OCH$_3$ |
| IIa-2 | (2) Cl, (4) Cl | | OCH$_3$ |

TABLE-continued

Examples of the compounds of the formula (IIa)

(IIa)

| Example No. | (Positions) (X¹)$_m$ | A¹ | R¹⁴ |
|---|---|---|---|
| IIa-3 | (2) Cl, (4) Cl | 1,3-dimethyl-5-methyl-5-(methoxycarbonyl)-pyrazoline | OC$_2$H$_5$ |
| IIa-4 | (2) Cl, (4) Cl | 1,3-dimethyl-5-methyl-5-(ethoxycarbonyl)-pyrazoline | OC$_2$H$_5$ |
| IIa-5 | (2) Cl | 1,3-dimethyl-5-phenyl-pyrazole | OCH$_3$ |
| IIa-6 | (2) Cl, (4) Cl | 1,3-dimethyl-5-phenyl-pyrazole | OCH$_3$ |
| IIa-7 | (2) F | 1,3-dimethyl-5-phenyl-pyrazole | OCH$_3$ |
| IIa-8 | (2) F | 1,3-dimethyl-5-(2-chlorophenyl)-pyrazole | OCH$_3$ |
| IIa-9 | (2) Cl, (4) Cl | 1,3-dimethyl-5-trichloromethyl-1,2,4-triazole | OC$_2$H$_5$ |
| IIa-10 | (2) Cl, (4) CF$_3$ | 1,3-dimethyl-5-phenyl-1,2,4-triazole | OCH$_3$ |
| IIa-11 | (2) Cl | 1,3-dimethyl-5-(2-fluorophenyl)-pyrazole | OCH$_3$ |
| IIa-12 | — | 3-methyl-5-phenyl-5-methyl-2-isoxazoline | OC$_2$H$_5$ |
| IIa-13 | (2) Cl, (4) Cl | 1,3-dimethyl-5-methyl-pyrazole | OC$_2$H$_5$ |
| IIa-14 | (2) Cl, (4) Cl | 1,3-dimethyl-5-isopropyl-pyrazole | OC$_2$H$_5$ |
| IIa-15 | (2) Cl, (4) Cl | 1,3-dimethyl-5-tert-butyl-pyrazole | OC$_2$H$_5$ |
| IIa-16 | (2) Cl, (4) Cl | 3-methyl-5-methyl-2-isoxazoline (CH$_2$ link) | OC$_2$H$_5$ |
| IIa-17 | (2) Cl, (4) Cl | 3,5-dimethyl-2-isoxazoline | OC$_2$H$_5$ |
| IIa-18 | — | 3-methyl-5-phenyl-5-methyl-2-isoxazoline | OH |

Examples of the compounds of the formula (IIb) which are very particularly preferred as herbicide safeners according to the invention are listed in the table below.

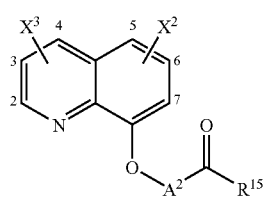

TABLE

Examples of the compounds of the formula (IIb)

| Example No. | (Position) X² | (Position) X³ | A² | R¹⁵ |
|---|---|---|---|---|
| IIb-1 | (5) Cl | — | CH₂ | OH |
| IIb-2 | (5) Cl | — | CH₂ | OCH₃ |
| IIb-3 | (5) Cl | — | CH₂ | OC₂H₅ |
| IIb-4 | (5) Cl | — | CH₂ | OC₃H₇-n |
| IIb-5 | (5) Cl | — | CH₂ | OC₃H₇-i |
| IIb-6 | (5) Cl | — | CH₂ | OC₄H₉-n |
| IIb-7 | (5) Cl | — | CH₂ | OCH(CH₃)C₅H₁₁-n |
| IIb-8 | (5) Cl | (2) F | CH₂ | OH |
| IIb-9 | (5) Cl | (2) Cl | CH₂ | OH |
| IIb-10 | (5) Cl | — | CH₂ | OCH₂CH=CH₂ |
| IIb-11 | (5) Cl | — | CH₂ | OC₄H₉-i |
| IIb-12 | (5) Cl | — | CH₂ | (structure) |
| IIb-13 | (5) Cl | — | (structure) | CH₂OCH₂CH=CH₂ |
| IIb-14 | (5) Cl | — | (structure) | OC₂H₅ |
| IIb-15 | (5) Cl | — | (structure) | OCH₃ |

Examples of the compounds of the formula (IIc) which are very particularly preferred as herbicide safeners according to the invention are listed in the table below.

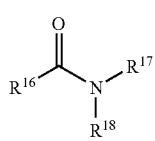

TABLE

Examples of the compounds of the formula (IIc)

| Example No. | R¹⁶ | N(R¹⁷, R¹⁸) |
|---|---|---|
| IIc-1 | CHCl₂ | N(CH₂CH=CH₂)₂ |
| IIc-2 | CHCl₂ | (2,2-dimethyloxazolidine) |
| IIc-3 | CHCl₂ | (2,2,5-trimethyloxazolidine) |
| IIc-4 | CHCl₂ | (spirocyclohexyl oxazolidine) |
| IIc-5 | CHCl₂ | (2,2-dimethyl-5-phenyloxazolidine) |
| IIc-6 | CHCl₂ | (3-methyl-benzoxazine) |
| IIc-7 | CHCl₂ | (2,2-dimethyl-5-furyloxazolidine) |

Examples of the compounds of the formula (IId) which are very particularly preferred as herbicide safeners according to the invention are listed in the table below.

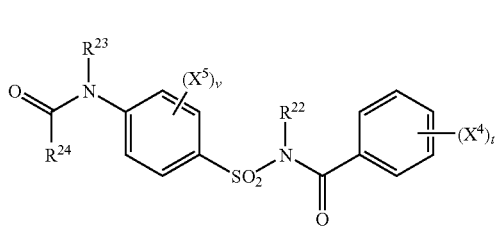

(IId)

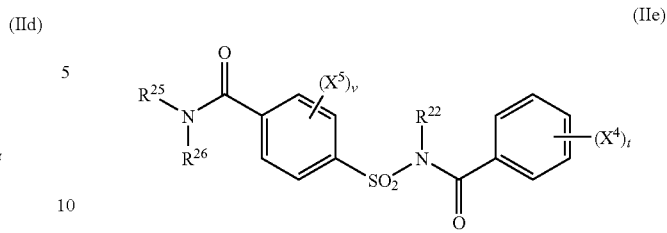

(IIe)

TABLE

Examples of the compounds of the formula (IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | NH-cyclopropyl | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in the table below.

TABLE

Examples of the compounds of the formula (IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | cyclopropyl | (2) $OCH_3$ (5) $CH_3$ | — |
| IIe-12 | H | $CH_3$ | $CH_3$ | (2) $OCH_3$ (5) $CH_3$ | — |

Most preferred as crop plant tolerance promoter compound [component (b′)] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective-herbicidal combinations according to the invention comprising in each case one active compound of the formula (I) and one of the safeners defined above are listed in the table below.

TABLE

Examples of the combinations according to the invention

| Active compounds of the formula (I) | Safeners |
|---|---|
| I-a | cloquintocet-mexyl |
| I-a | fenchlorazole-ethyl |
| I-a | isoxadifen-ethyl |
| I-a | mefenpyr-diethyl |
| I-a | furilazole |
| I-a | fenclorim |
| I-a | cumyluron |
| I-a | daimuron/dymron |
| I-a | dimepiperate |
| I-a | IIe-11 |
| I-a | IIe-5 |
| I-b | cloquintocet-mexyl |
| I-b | fenchlorazole-ethyl |
| I-b | isoxadifen-ethyl |
| I-b | mefenpyr-diethyl |
| I-b | furilazole |
| I-b | fenclorim |
| I-b | cumyluron |
| I-b | daimuron/dymron |
| I-b | dimepiperate |
| I-b | IIe-11 |
| I-b | IIe-5 |
| I-c | cloquintocet-mexyl |
| I-c | fenchlorazole-ethyl |
| I-c | isoxadifen-ethyl |
| I-c | mefenpyr-diethyl |
| I-c | furilazole |
| I-c | fenclorim |
| I-c | cumyluron |
| I-c | daimuron/dymron |
| I-c | dimepiperate |
| I-c | IIe-5 |
| I-c | IIe-11 |
| I-d | cloquintocet-mexyl |
| I-d | fenchlorazole-ethyl |
| I-d | isoxadifen-ethyl |
| I-d | mefenpyr-diethyl |
| I-d | furilazole |
| I-d | fenclorim |
| I-d | cumyluron |
| I-d | daimuron/dymron |
| I-d | dimepiperate |
| I-d | IIe-11 |
| I-d | IIe-5 |
| I-e | cloquintocet-mexyl |
| I-e | fenchlorazole-ethyl |
| I-e | isoxadifen-ethyl |
| I-e | mefenpyr-diethyl |
| I-e | furilazole |
| I-e | fenclorim |
| I-e | cumyluron |
| I-e | daimuron/dymron |
| I-e | dimepiperate |
| I-e | IIe-5 |
| I-e | IIe-11 |
| I-f | cloquintocet-mexyl |
| I-f | fenchlorazole-ethyl |
| I-f | isoxadifen-ethyl |
| I-f | mefenpyr-diethyl |
| I-f | furilazole |
| I-f | fenclorim |
| I-f | cumyluron |
| I-f | daimuron/dymron |
| I-f | dimepiperate |
| I-f | IIe-5 |
| I-f | IIe-11 |
| I-g | cloquintocet-mexyl |
| I-g | fenchlorazole-ethyl |
| I-g | isoxadifen-ethyl |
| I-g | mefenpyr-diethyl |
| I-g | furilazole |
| I-g | fenclorim |
| I-g | cumyluron |
| I-g | daimuron/dymron |
| I-g | dimepiperate |
| I-g | IIe-5 |
| I-g | IIe-11 |

It has now surprisingly been found that the above-defined active compound combinations of substituted tetramic acid derivatives of the formula (I) and safeners (antidotes) from the group (b') set out above combine very good useful plant tolerance with a high herbicidal activity and can be used in various crops, in particular in cereals (especially wheat), but also in soya, potatoes, maize and rice, for selective weed control.

In this context it is considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of substituted tetramic acid derivatives on the crop plants, without at the same time having any critical adverse effect on the herbicidal activity against the weeds.

Emphasis may be given here to the particularly advantageous effect of the particularly preferred and most preferred combination partners from group (b'), particularly with regard to the gentle treatment of cereal plants, such as wheat, barley and rye, for example, but also maize and rice, as crop plants.

Using, for example, according to process (A) ethyl N-[(2-methoxy-4-methyl-6-ethyl)phenylacetyl]-1-amino-4-ethoxycyclohexanecarboxylate as starting material, the course of the process according to the invention can be represented by the reaction scheme below:

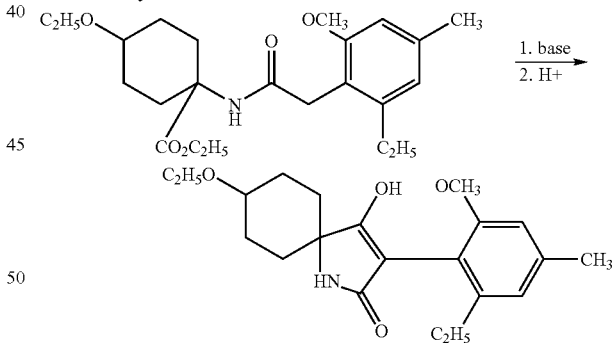

Using, for example, according to process (Bα) 3-[(2-methoxy-4-methyl-6-ethyl)phenyl]-1-azaspiro[4,5]decane-2,4-dione and pivaloyl chloride as starting materials, the course of the process according to the invention can be represented by the reaction scheme below:

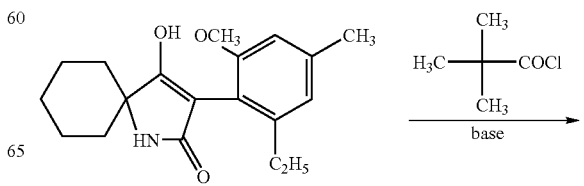

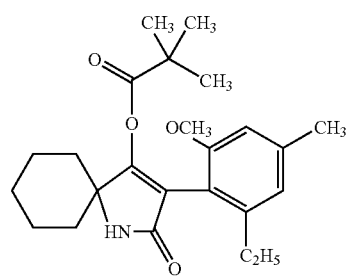

Using, for example, according to process (B) (variant β) 8-methoxy-3-[(2-methoxy-4-methyl-6-ethyl)phenyl]-1-azaspiro[4,5]decane-2,4-dione and acetic anhydride as starting materials, the course of the process according to the invention can be represented by the reaction scheme below:

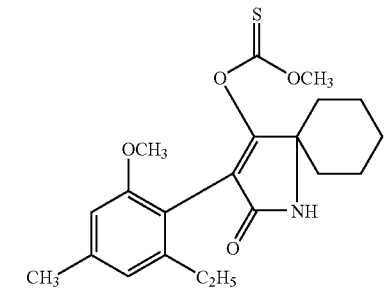

Using, for example, according to process (C) 3-[2-methoxy-4-methyl-6-ethyl)phenyl]-1-azaspiro[4,5]dec-3-ane-2,4-dione and ethyl chloroformate as starting materials, the course of the process according to the invention can be represented by the reaction scheme below:

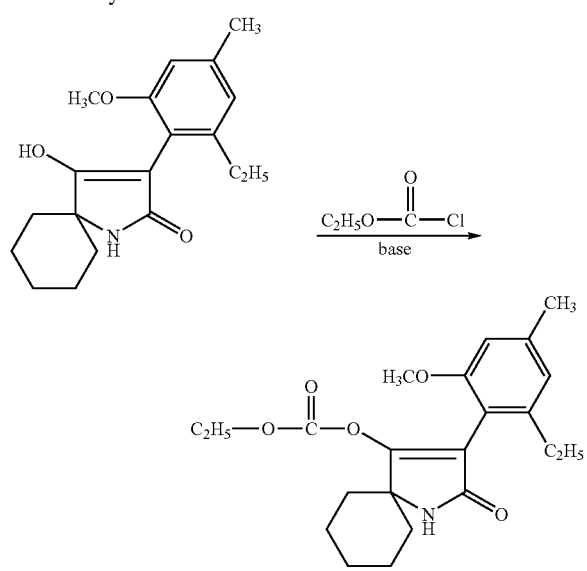

Using, for example, according to process (D), variant α, 3-[(2-methoxy-4-methyl-6-ethyl)phenyl]-1-azaspiro[4,5]decane-2,4-dione and methyl chloromonothioformate as starting materials, the course of the reaction can be represented as follows:

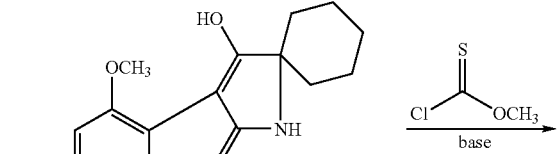

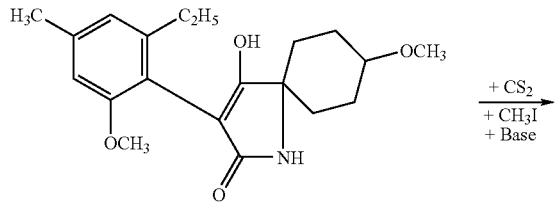

Using, for example, according to process (D), variant β, 8-methoxy-3-[(2-methoxy-4-methyl-6-ethyl)-phenyl]-1-azaspiro[4,5]decane-2,4-dione, carbon disulfide and methyl iodide as starting components, the course of the reaction can be represented as follows:

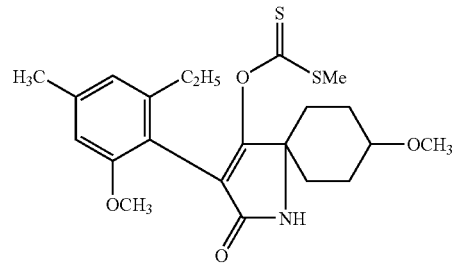

Using, for example, according to process (E) 3-[(2-methoxy-4-methyl-6-ethyl)phenyl]-1-azaspiro[4,5]decane-2,4-dione and methanesulfonyl chloride as starting material, the course of the reaction can be represented by the reaction scheme below:

-continued

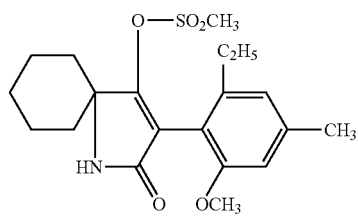

Using, for example, according to process (F) 3-[(2-methoxy-4-methyl-6-ethyl)phenyl]-1-azaspiro[4,5]decane-2,4-dione and 2,2,2-trifluoroethyl methanethiophosphonyl chloride as starting materials, the course of the reaction can be represented by the reaction scheme below:

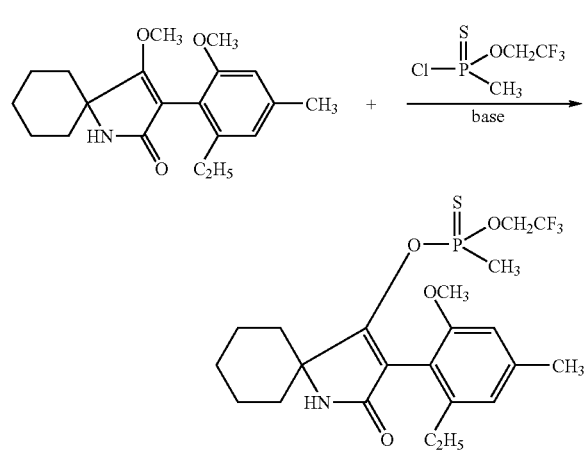

Using, for example, according to process (G) 8-methoxy-3-[(2-methoxy-4-methyl-6-ethyl)phenyl]-1-azaspiro[4,5]decane-2,4-dione and NaOH as components, the course of the process according to the invention can be represented by the reaction scheme below:

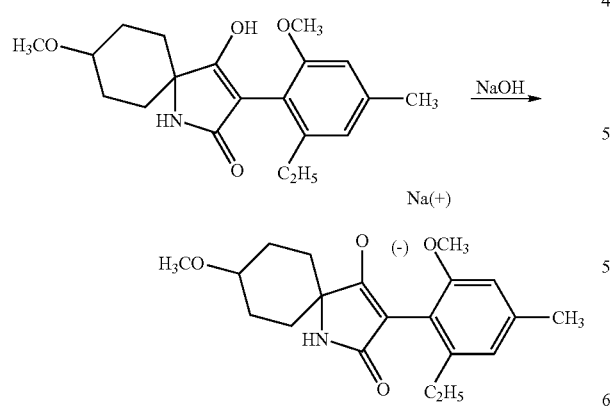

Using, for example, according to process (H) variant α, 3-[(2-methoxy-4-methyl-6-ethyl)phenyl]-1-azaspiro[4,5]decane-2,4-dione and ethyl isocyanate as starting materials, the course of the reaction can be represented by the reaction scheme below:

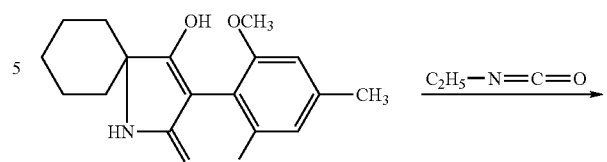

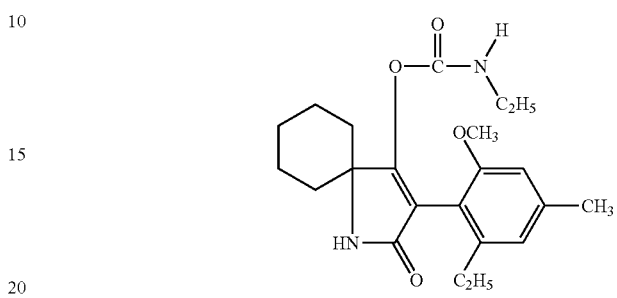

Using, for example, according to process (H) variant β, 8-methoxy-3-[(2-methoxy-4-methyl-6-ethyl)-phenyl]-1-azaspiro[4,5]decane-2,4-dione and dimethylcarbamoyl chloride as starting materials, the course of the reaction can be represented by the scheme below:

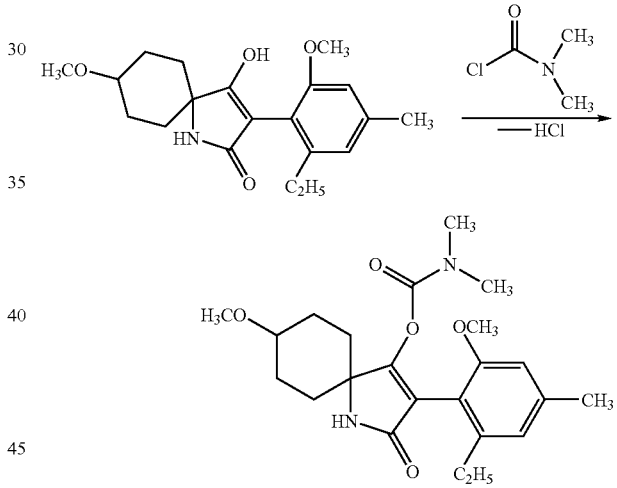

The compounds, required as starting materials in process (A) according to the invention, of the formula (II)

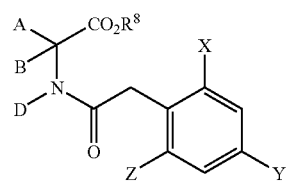

(II)

in which
A, B, D, X, Y, Z and $R^8$ are as defined above
are novel.

The acylamino acid esters of the formula (II) are obtained, for example, when amino acid derivatives of the formula (XIV),

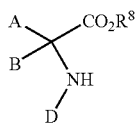
(XIV)

in which
A, B, D and R⁸ are as defined above
are acylated with substituted phenylacetyl halides of the formula (XV),

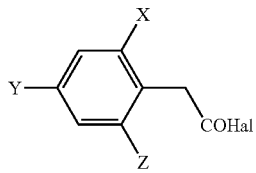
(XV)

in which
X, Y and Z are as defined above and
Hal represents chlorine or bromine,
(Chem. Reviews 52, 237-416 (1953); Bhattacharya, Indian J. Chem. 6, 341-5, 1968, patent literature cited at the outset, for example WO 97/02243)

or when acylamino acids of the formula (XVI),

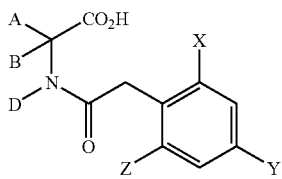
(XVI)

in which
A, B, D, X, Y and Z are as defined above
are esterified (Chem. Ind. (London) 1568 (1968)).

The compounds of the formula (XVI),

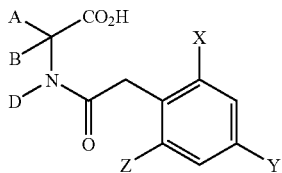
(XVI)

in which
A, B, D, X, Y and Z are as defined above
are likewise novel.

The compounds of the formula (XVI) are obtained when amino acids of the formula (XVII),

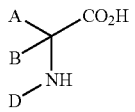
(XVII)

in which
A, B and D are as defined above
are acylated with substituted phenylacetyl halides of the formula (XV),

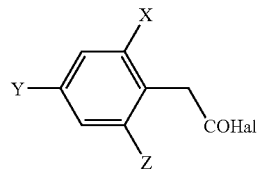
(XV)

in which
X, Y and Z are as defined above and
Hal represents chlorine or bromine according to Schotten-Baumann (Organikum, VEB Deutscher Verlag der Wissenschaften, Berlin 1977, p. 505).

Some of the compounds of the formula (XV) are novel and can be prepared by processes known in principle (WO 97/02243).

The compounds of the formula (XV) are obtained, for example, when substituted phenylacetic acids of the formula (XVIII),

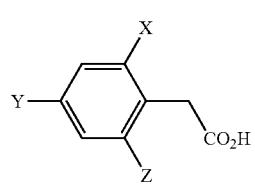
(XVIII)

in which
X, Y and Z are as defined above are reacted with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons, such as toluene or methylene chloride) at temperatures of from −20° C. to 150° C., preferably from −10° C. to 100° C.

The compounds of the formula (XVIII) are novel.

The compounds of the formula (XVIII) are obtained, for example, when substituted phenylacetic esters of the formula (XIX),

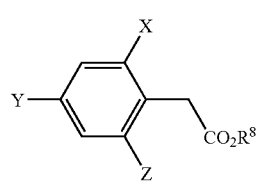
(XIX)

in which
X, Y, Z and R⁸ are as defined above are hydrolyzed in the presence of an acid (for example an inorganic acid, such as hydrochloric acid) or a base (for example an alkali metal hydroxide, such as sodium hydroxide or potassium hydroxide) and, if appropriate, a diluent (for example an aqueous alcohol, such as methanol or ethanol) at temperatures between 0° C. and 150° C., preferably between 20° C. and 100° C.

The compounds of the formula (XIX) are likewise novel and can be prepared by processes known in principle (WO 04/080962).

The compounds of the formula (XIX)

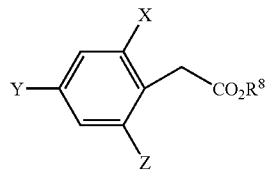
(XIX)

in which
X, Y, Z and $R^8$ are as defined above
are obtained, for example, when phenylacetic esters of the formula (XIX-a)

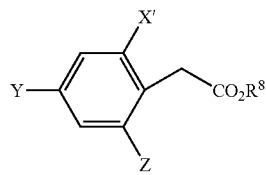
(XIX-a)

in which
$R^8$, Y and Z are as defined above and
X' represents halogen (in particular bromine)
are reacted in the presence of an alcohol, in the presence of a base and, if appropriate, in the presence of a catalyst (preferably copper salts, such as, for example copper(I) bromide).

Some of the compounds of the formula (XIX-a) are known and can be prepared by processes known in principle (WO 05/044796).

Some of the compounds of the formulae (XIV) and (XVII) are known, and/or they can be prepared by processes known in principle (see, for example, Compagnon, Miocque Ann. Chim. (Paris) [14] 5, pp. 11-22, 23-27 (1970)).

The substituted cyclic aminocarboxylic acids of the formula (XVII) in which A and B form a ring can generally be obtained by the Bucherer-Bergs synthesis or by the Strecker synthesis, where they are in each case obtained by different isomeric forms. Thus, the conditions of the Bucherer-Bergs synthesis give predominantly the isomers (for simplicity reasons referred to as β hereinbelow) in which the radicals R and the carboxyl group are in equatorial positions, while the conditions of the Strecker synthesis give predominantly the isomers (for simplicity reasons referred to as α hereinbelow) where the amino group and the radicals R are in equatorial positions.

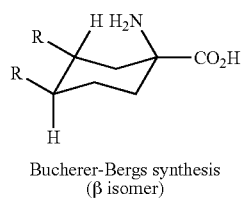
Bucherer-Bergs synthesis
(β isomer)

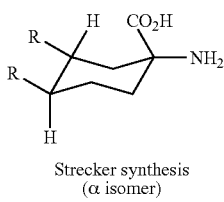
Strecker synthesis
(α isomer)

The 3-alkoxy-1-amino-cyclohexanecarboxylic acids (XVII) in which A and B form a ring are generally known from DE-A-04 030 753 and are generally obtained by means of the Bucherer-Bergs synthesis or the Strecker synthesis, where they are obtained in each case in different isomeric forms. Hereinbelow, for the sake of simplicity, the isomers in which the 3-substituent (R) and the amino group are equatorial/axial or axial/equatorial are referred to as β. For the sake of simplicity, the isomers in which the amino group and the 3-substituent (R) are equatorial/equatorial or axial/axial are referred to as α hereinbelow.

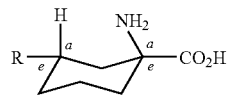
Example: β isomer

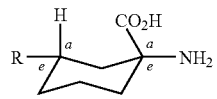
Example: α isomer (L. Munday, J. Chem. Soc. 4372 (1961); J. T. Eward, C. Jitrangeri, Can. J. Chem. 53, 3339 (1975)).

Furthermore, the starting materials, used in the above process (A), of the formula (II),

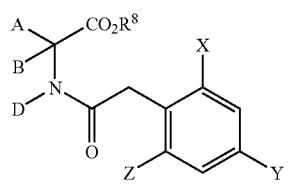
(II)

in which
A, B, D, X, Y, Z and $R^8$ are as defined above
can be prepared by reacting aminonitriles of the formula (XXI),

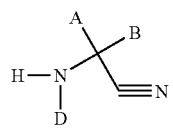
(XXIII)

in which
A, B and D are as defined above
with substituted phenylacetyl halides of the formula (XV),

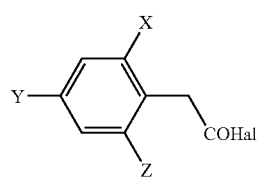
(XV)

in which
X, Y, Z and Hal are as defined above
to give compounds of the formula (XXIV),

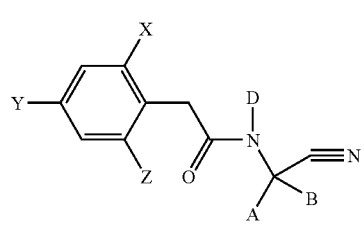
(XXIV)

in which
A, B, D, X, Y and Z are as defined above
and then subjecting these to an acidic alcoholysis.

The compounds of the formula (XXIV) are likewise novel.

The acid halides of the formula (III), carboxylic anhydrides of the formula (IV), chloroformic esters The process (A) according to the invention is generally carried out under atmospheric pressure.

When carrying out the process (A) according to the invention, the reaction component of the formula (II) and the deprotonating base are generally employed in equimolar to about doubly equimolar amounts. However, it is also possible to use a relatively large excess (up to 3 mol) of one component or the other.

The process (Bα) is characterized in that compounds of the formula (I-a) are in each case reacted with carbonyl halides of the formula (III), if appropriate in the presence of a diluent and if appropriate in the presence of an acid binder.

Suitable diluents for use in the process (Bα) according to the invention are all solvents which are inert to the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane. The hydrolytic stability of the acid halide permitting, the reaction can also be carried out in the presence of water.

Suitable acid binders for the reaction according to process (Bα) according to the invention are all customary acid acceptors. Preference is given to using tertiary amines, such as triethylamine, pyridine, diazabicyclooctane (DABCO), diazabicycloundecane (DBU), diazabicyclononene (DBN), Hünig base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

The reaction temperature in the process (Bα) according to the invention can be varied within a relatively wide range. In general, the process is carried out at temperatures between −20° C. and +150° C., preferably between 0° C. and 100° C.

When carrying out the process variant (Bα) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process (Bβ) is characterized in that compounds of the formula (I-a) are in each case reacted or chloroformic thioesters of the formula (V), chloromonothioformic esters or chlorodithioformic esters of the formula (VI), alkyl halides of the formula (VII), sulfonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII) furthermore required as starting materials for carrying out the processes (B), (C), (D), (E), (F), (G) and (H) according to the invention are generally known compounds of organic or inorganic chemistry.

In addition, the compounds of the formulae (XIV) and (XVII) are known from the patent applications cited at the outset and/or they can be prepared by the methods given therein.

The process (A) is characterized in that compounds of the formula (II) in which A, B, D, X, Y, Z and $R^8$ are as defined above are subjected to an intramolecular condensation in the presence of a diluent and in the presence of a base.

Suitable for use as diluents for use in the process (A) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl-($C_8$-$C_{10}$)ammonium chloride) or TDA 1 (=tris(methoxyethoxyethyl)amine). It is furthermore possible to use alkali metals, such as sodium or potassium. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide, may be used.

When carrying out the process (A) according to the invention, the reaction temperature may be varied within a relatively wide range. In general, the process is carried out at temperatures between 0° C. and 250° C., preferably between 50° C. and 150° C. with carboxylic anhydrides of the formula (IV), if appropriate in the presence of a diluent and if appropriate in the presence of an acid binder.

Suitable diluents for use in the process (Bβ) according to the invention are preferably those diluents which are also preferred when acid halides are used. Besides, it is also possible for excess carboxylic anhydride to act simultaneously as diluent.

Suitable optional acid binders for process (Bβ) are preferably those acid binders which are also preferred when acid halides are used.

The reaction temperature in the process (Bβ) according to the invention may be varied within a relatively wide range. In general, the process is carried out at temperatures between −20° C. and +150° C., preferably between 0° C. and 100° C.

When carrying out the process (Bβ) according to the invention, the starting materials of formula (I-a) and the carboxylic anhydride of the formula (IV) are generally each employed in approximately equivalent amounts. However, it is also possible to use a relatively large excess (up to 5 mol) of the carboxylic anhydride. Work-up is carried out by customary methods.

In general, the diluent and excess carboxylic anhydride and the carboxylic acid formed are removed by distillation or by washing with an organic solvent or with water.

The process (C) is characterized in that compounds of the formula (I-a) are in each case reacted with chloroformic esters or chloroformic thioesters of the formula (V), if appropriate in the presence of a diluent and if appropriate in the presence of an acid binder.

Suitable acid binders for the process (C) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (C) according to the invention are all solvents which are inert to the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulfoxide and sulfolane.

When carrying out the process (C) according to the invention, the reaction temperature can be varied to within a relatively wide range. In general, the reaction temperature is between $-20°$ C. and $+100°$ C., preferably between $0°$ C. and $50°$ C.

The process (C) according to the invention is generally carried out under atmospheric pressure.

When carrying out the process (C) according to the invention, the starting materials of the formula (I-a) and the appropriate chloroformic ester or chloroformic thioester of the formula (V) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (D) according to the invention is characterized in that compounds of the formula (I-a) are in each case reacted with (Dα) compounds of the formula (VI) in the presence of a diluent and if appropriate in the presence of an acid binder or (Dβ) carbon disulfide and then with alkyl halides of the formula (VII), if appropriate in the presence of a diluent and if appropriate in the presence of a base.

In preparation process (Dα), about 1 mol of chloromonothioformic ester or chlorodithioformic ester of the formula (VI) is reacted per mole of starting material of the formula (I-a) at from $0$ to $120°$ C., preferably at from $20$ to $60°$ C.

Suitable diluents which are added, if appropriate, are all inert polar organic solvents, such as ethers, esters, amides, sulfones, sulfoxides, and also halogenated alkanes.

Preference is given to using dimethyl sulfoxide, ethyl acetate, tetrahydrofuran, dimethylformamide or methylene chloride.

If, in a preferred embodiment, the enolate salt of the compound (I-a) is prepared by addition of strong deprotonating agents, such as, for example, sodium hydride or potassium tert-butoxide, the further addition of acid binders may be dispensed with.

If acid binders are used, these are customary inorganic or organic bases, for example sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

In preparation process (Dβ), in each case the equimolar amount or an excess of carbon disulfide is added per mole of starting material of the formula (I-a). The process is preferably out at temperatures of from $0$ to $50°$ C. and in particular from $20$ to $30°$ C.

In many cases, it is expedient to prepare initially the corresponding salt from the compounds of the formula (I-a) by adding a base (such as, for example, potassium tert-butoxide or sodium hydride). In each case, the compound (I-a) is reacted with carbon disulfide until the formation of the intermediate has ended, for example after a number of hours of stirring at room temperature.

Suitable for use as bases in the process (Dβ) are all customary proton acceptors. Preference is given to using alkali metal hydrides, alkali metal alkoxides, alkali metal or alkaline earth metal carbonates or bicarbonates, or nitrogen bases. Sodium hydride, sodium methoxide, sodium hydroxide, calcium hydroxide, potassium carbonate, sodium bicarbonate, triethylamine, dibenzylamine, diisopropylethylamine, pyridine, quinoline, diazabicyclooctane (DABCO), diazabicyclononene (DBN) and diazabicycloundecene (DBU) may be mentioned by way of example.

Suitable for use as diluents in this process are all customary solvents.

Preference is given to using aromatic hydrocarbons, such as benzene or toluene, alcohols, such as methanol, ethanol, isopropanol or ethylene glycol, nitrites, such as acetonitrile, ethers, such as tetrahydrofuran or dioxane, amides, such as dimethylformamide, or other polar solvents, such as dimethyl sulfoxide or sulfolane.

The further reaction with the alkyl halide of the formula (VII) is preferably carried out at from $0$ to $70°$ C. and in particular at from $20$ to $50°$ C. Here, at least an equimolar amount of alkyl halide is used.

The process is carried out at atmospheric pressure or under elevated pressure, preferably at atmospheric pressure.

Work-up is again carried out by customary methods.

The process (E) according to the invention is characterized in that compounds of the formula (I-a) are in each case reacted with sulfonyl chlorides of the formula (VII), if appropriate in the presence of a diluent and if appropriate in the presence of an acid binder.

In preparation process (E), about 1 mol of sulfonyl chloride of the formula (VI) is reacted per mole of starting material of the formula (I-a), at from $-20$ to $150°$ C., preferably at from $-20$ to $70°$ C.

The process (E) is preferably carried out in the presence of a diluent.

Suitable diluents are all inert polar organic solvents, such as ethers, esters, amides, nitriles, sulfones, sulfoxides or halogenated hydrocarbons, such as methylene chloride.

Preference is given to using dimethyl sulfoxide, tetrahydrofuran, ethyl acetate, dimethylformamide, methylene chloride.

If, in a preferred embodiment, the enolate salt of the compound (I-a) is prepared by adding strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with phosphorus compounds of the formula (IX), if appropriate in the presence of a diluent and if appropriate in the presence of an acid binder.

In preparation process (F), to obtain compounds of the formula (I-e), 1 to 2, preferably 1 to 1.3, mol of the phosphorus compound of the formula (IX) are employed per mole of the compound (I-a), at temperatures between −40° C. and 150° C., preferably between −10 and 110° C.

The process (F) is preferably carried out in the presence of a diluent.

Suitable diluents are all inert polar organic solvents, such as ethers, esters, amides, nitriles, sulfides, sulfones, sulfoxides, etc.

Preference is given to using acetonitrile, ethyl acetate, dimethyl sulfoxide, tetrahydrofuran, dimethylformamide, methylene chloride.

Suitable optional acid binders are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The end products are preferably purified by crystallization, chromatographic purification or "incipient distillation", i.e. removal of the volatile components under reduced pressure.

The process (G) is characterized in that compounds of the formula (I-a) are in each case reacted with metal hydroxides or metal alkoxides of the formula (X) or amines of the formula (XI), if appropriate in the presence of a diluent.

Suitable diluents for use in the process (G) according to the invention are, preferably, ethers, such as tetrahydrofuran, dioxane, diethyl ether, or else alcohols, such as methanol, ethanol, isopropanol, and also water. The process (G) according to the invention is generally carried out under atmospheric pressure. The reaction temperatures are generally between −20° C. and 100° C., preferably between 0° C. and 50° C.

The process (H) according to the invention is characterized in that compounds of the formula (I-a) are in each case reacted with (Hα) compounds of the formula (XII), if appropriate in the presence of a diluent and if appropriate in the presence of a catalyst, or (Hβ) with compounds of the formula (XIII), if appropriate in the presence of a diluent and if appropriate in the presence of an acid binder.

In preparation process (Hα), about 1 mol of isocyanate of the formula (XIII) is reacted per mole of starting material of the formula (I-a), at from 0 to 100° C., preferably from 20 to 50° C.

The process (Hα) is preferably carried out in the presence of a diluent.

Suitable diluents are all inert organic solvents, such as ethers, esters, amides, nitriles, sulfones or sulfoxides.

If appropriate, catalysts may be added to promote the reaction. Very advantageous for use as catalysts are organotin compounds, such as, for example, dibutyltin dilaurate.

The process is preferably carried out at atmospheric pressure.

In preparation process (Hβ), about 1 mol of carbamoyl chloride of the formula (XIII) is reacted per mole of starting material of the formula (I-a), at from 0 to 150° C., preferably from 20 to 70° C.

Suitable optional diluents are all inert polar organic solvents, such as ethers, esters, amides, sulfones, sulfoxides or halogenated hydrocarbons.

Preference is given to using dimethyl sulfoxide, ethyl acetate, tetrahydrofuran, dimethylformamide or methylene chloride.

If, in a preferred embodiment, the enolate salt of the compound (I-a) is prepared by adding strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The process (I) is characterized in that compounds of the formula (I-a') in which A, B, D, Y, Z, $R^1$, $R^2$, $R^3$, $R^4$, $R^5$, $R^6$ and $R^7$ are as defined above and X' represents halogen, particularly preferably bromine, are subjected to an exchange reaction with alcohols of the formula (XXV) in which X is as defined above, in the presence of a copper salt and in the presence of a base.

Suitable diluents for use in the process (I) according to the invention are, for example, optionally halogenated aliphatic, alicyclic or aromatic hydrocarbons, such as, for example, benzine, benzene, toluene, xylene, petroleum ether, hexane, cyclohexane, chlorobenzene, dichlorobenzene, ethers, such as diethyl ether, diisopropyl ether, dioxane, tetrahydrofuran or ethylene glycol dimethyl ether or ethylene glycol diethyl ether; amides, such as, for example, N,N-dimethylformamide, N,N-dimethylacetamide, N-methylformanilide, N-methylpyrrolidone or hexamethylphosphoric triamide; esters, such as methyl acetate or ethyl acetate, or mixtures of such solvents. Preference is given to using N,N-dimethylformamide.

Suitable bases for use in the process (I) according to the invention are alkali metal and/or alkaline earth metal carbonates, alkoxides and/or hydroxides, particular preference being given to sodium methoxide, sodium ethoxide, sodium propoxide, sodium butoxide, potassium tert-butoxide, potassium amylate.

The copper salts used in the process (I) according to the invention are copper(I) salts, such as, for example, CuBr, CuI.

When carrying out the process (I) according to the invention, the reaction temperatures can be varied within a relatively wide range. In general, the process is carried out at temperatures of from 0 to 250° C., preferably at from 30 to 200° C.; very particularly preferably at from 50 to 150° C.

The process (I) according to the invention is generally carried out under atmospheric pressure.

When carrying out the process (I) according to the invention, the reaction components of the formulae (I-1'-a') and (XXV) are generally employed in equimolar amounts. However, it is also possible to use a relatively large excess of the alcohols of the formula (XXV), or to use them as solvent. The bases are generally employed in a molar ratio of from 1:1 to 30:1, preferably from 2:1 to 10:1. The copper salts are generally employed in a molar ratio of from 0.01:1 to 1:1, preferably from 0.05:1 to 0.5:1.

The active compounds are well tolerated by plants, have favorable homeotherm toxicity and are environmentally friendly; they are suitable for protecting plants and plant organs, for increasing harvest yields, for improving the quality of the harvested material and for controlling animal pests, in particular insects, arachnids and nematodes encountered in agriculture, in forests, in gardens and leisure facilities, in the protection of stored products and materials and in the hygiene sector. They are preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella accidentalis.*

From the order of the Heteroptera, for example, *Eurygaster* spp., *Dysdercus* intermedius, Piesma quadrata, Cimex lectularius, Rhodnius prolixus and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds according to the invention may also be used in certain concentrations or application rates to act as herbicides and microbicides, for example as fungicides, antimycotics and bactericides. If appropriate, they can also be employed as intermediates or precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides or insecticides, for example in order to widen the spectrum of action or to prevent the development of resistances in this way. In many cases, synergistic effects result, i.e. the activity of the mixture exceeds the activity of the individual components.

Compounds which are suitable as mixing partners are, for example, the following:

Fungicides:

2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulfonyl)amino]butanamide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate;

and copper salts and preparations, such as Bordeaux mixture; copper hydroxide; copper naphthenate; copper oxychloride; copper sulfate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:
1. Acetylcholine esterase (AChE) inhibitors
1.1 Carbamates, for example
   alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb
   Triazamates
1.2 Organophosphates, for example
   acephate, azamethiphos, azinphos (-methyl, -ethyl), bromophos-ethyl, brom-fenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion
2. Sodium channel modulators/voltage-dependent sodium channel blockers
2.1 Pyrethroids, for example
   acrinathrin, allethrin (d-cis-trans, d-trans), beta-cyfluthrin, bifenthrin, bioallethrin, bioallethrin-S cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
   DDT
2.2 Oxadiazines, for example indoxacarb
3. Acetylcholine receptor agonists/antagonists
3.1 Chloronicotinyls, for example
   acetamiprid, clothianidin, dinotefuran, imidacloprid, nitenpyram, nithiazine, thiacloprid, thiamethoxam
3.2 Nicotine, bensultap, cartap
4. Acetylcholine receptor modulators
4.1 Spinosyns, for example spinosad
5. GABA-controlled chloride channel antagonists
5.1 Cyclodiene organochlorines, for example
   camphechlor, chlordane, endosulfan, gamma-HCH, HCH, heptachlor, lindane, methoxychlor
5.2 Fiproles, for example
   acetoprole, ethiprole, fipronil, vaniliprole
6. Chloride channel activators
6.1 Mectins, for example
   avermectin, emamectin, emamectin-benzoate, ivermectin, milbemycin
7. Juvenile hormone mimetics, for example
   diofenolan, epofenonane, fenoxycarb, hydroprene, kinoprene, methoprene, pyriproxifen, triprene
8. Ecdyson agonists/disruptors
8.1 Diacylhydrazines, for example
   chromafenozide, halofenozide, methoxyfenozide, tebufenozide
9. Chitin biosynthesis inhibitors
9.1 Benzoylureas, for example
   bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
9.2 Buprofezin
9.3 Cyromazine
10. Oxidative phosphorylation inhibitors, ATP disruptors
10.1 Diafenthiuron
10.2 Organotins, for example azocyclotin, cyhexatin, fenbutatin-oxide
11. Oxidative phosphorylation decouplers acting by interrupting the H-proton gradient
11.1 Pyrroles, for example chlorfenapyr
11.2 Dinitrophenols, for example binapacyrl, dinobuton, dinocap, DNOC
12. Side-I electron transport inhibitors
12.1 METIs, for example fenazaquin, fenpyroximate, pyrimidifen, pyridaben, tebufenpyrad, tolfenpyrad
12.2 Hydramethylnon
12.3 Dicofol
13. Side-II electron transport inhibitors
   Rotenone
14. Side-III electron transport inhibitors
   Acequinocyl, fluacrypyrim
15. Microbial disruptors of the insect gut membrane *Bacillus thuringiensis* strains
16. Fat synthesis inhibitors
   Tetronic acids, for example
      spirodiclofen, spiromesifen
   Tetramic acids, for example
      3-(2,5-dimethylphenyl)-8-methoxy-2-oxo-1-azaspiro[4.5]dec-3-en-4-yl ethyl carbonate (aka: carbonic acid, 3-(2,5-dimethylphenyl)-8-methoxy-2-oxo-1-azaspiro[4.5]dec-3-en-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1)
17. Carboxamides, for example flonicamid
18. Octopaminergic agonists, for example amitraz
19. Inhibitors of magnesium-stimulated ATPase, for example propargite
20. BDCAs, for example N-2-[1,1-dimethyl-2-(methylsulfonyl)ethyl]-3-iodo-N1-[2-methyl-4-[1,2,2,2-tetrafluoro-1-(trifluoromethyl)ethyl]phenyl]-1,2-benzenedicarboxamide (CAS-Reg.-No.: 272451-65-7)

21. Nereistoxin analogues, for example thiocyclam hydrogen oxalate, thiosultap-sodium
22. Biologicals, hormones or pheromones, for example azadirachtin, *Bacillus* spec., *Beauveria* spec., codlemone, *Metarrhizium* spec., *Paecilomyces* spec., thuringiensin, *Verticillium* spec.
23. Active compounds with unknown or unspecific mechanisms of action
23.1 Fumigants, for example
    aluminium phosphide, methyl bromide, sulfuryl fluoride
23.2 Selective antifeedants, for example
    cryolite, flonicamid, pymetrozine
23.3 Mite growth inhibitors, for example
    clofentezine, etoxazole, hexythiazox
23.4 Amidoflumet, benclothiaz, benzoximate, bifenazate, bromopropylate, buprofezin, quino-methionate, chlordimeform, chlorobenzilate, chloropicrin, clothiazoben, cycloprene, di-cyclanil, fenoxacrim, fentrifanil, flubenzimine, flufenerim, flutenzin, gossyplure, hydra-methylnone, japonilure, metoxadiazone, petroleum, piperonyl butoxide, potassium oleate, pyridalyl, sulfluramid, tetradifon, tetrasul, triarathene, verbutin, and also products which comprise insecticidal plant extracts, nematodes, fungi or viruses.

A mixture with other known active compounds, such as herbicides, or with fertilizers and growth regulators, safeners and/or semiochemicals is also possible.

When used as insecticides in their commercially available formulations and in the use forms prepared with these formulations, the active compounds according to the invention can furthermore be present in the form of a mixture with synergists. Synergists are compounds by which the activity of the active compounds is increased without it being necessary for the synergist added to be active itself.

When used as insecticides in their commercially available formulations and in the use forms prepared with these formulations, the active compounds according to the invention can furthermore be present in the form of a mixture with inhibitors which reduce the degradation of the active compound after application in the habitat of the plant, on the surface of parts of plants or in plant tissues.

The active compound content of the use forms prepared from the commercially available formulations can vary within broad ranges. The active compound concentration of the use forms can be from 0.0000001 up to 95% by weight of active compound, preferably between 0.0001 and 1% by weight.

They are applied in a customary manner adapted to suit the use forms.

When used against hygiene pests and pests of stored products, the active compound is distinguished by excellent residual action on wood and clay as well as good stability to alkali on limed substrates.

As already mentioned above, it is possible to treat all plants and their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetic modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such traits are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, tobacco, oilseed rape and fruit plants (with the fruits apples, pears, citrus fruits and grapes), with particular emphasis on maize, soybeans, potatoes, cotton, tobacco, and oilseed rape. Traits which are especially emphasized are the increased defense of the plants against insects, arachnids, nematodes and slugs and snails, owing to toxins being formed in the plants, in particular toxins which are generated in the plants by the genetic material of *Bacillus thuringiensis* (for example by the genes CryIA(a), CryIA(b), CryIA(c), CryIIA, CryIIA, CryIIIB2, Cry9c Cry2Ab, Cry3Bb and CryIF and their combinations; hereinbelow "Bt plants"). Other traits which are particularly emphasized are the increased defense of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulfonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula I or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds according to the invention are not only active against plant, hygiene and stored-product pests, but also, in the veterinary medicine sector, against animal parasites (ectoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the sub-class of the Acaria (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec., Dinoderus minutus.*

Dermapterans, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina*.

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odor-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder.

Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulfonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid and triflumuron, chlothianidin, spinosad, tefluthrin, and fungicides, such as epoxyconazole, hexaconazole, azaconazole, propiconazole, tebuconazole, cyproconazole, metconazole, imazalil, dichlorfluanid, tolylfluanid, 3-iodo-2-propynylbutyl carbamate, N-octyl-isothiazolin-3-one and 4,5-dichloro-N-octylisothiazolin-3-one.

The compounds according to the invention can at the same time be employed for protecting objects which come into contact with sea water or brackish water, in particular hulls, screens, nets, buildings, moorings and signaling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulfides, tri-n-butyltin laurate, tri-n-butyltin chloride, copper(I) oxide, triethyltin chloride, tri-n-butyl-(2-phenyl-4-chlorophenoxy)tin, tributyltin oxide, molybdenum disulfide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tri-butyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propynyl butyl-carbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb; Fe chelates;

or conventional antifouling active compounds such as 4,5-dichloro-2-octyl-4-isothiazolin-3-one, diiodomethylparatryl sulfone, 2-(N,N-dimethyl-thiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl)-pyridine, 2,4,5,6-tetrachloroisophthalonitrile, tetramethylthiuram disulfide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the theological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used in the household insecticides sector alone or in combination with other suitable active compounds such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations, such as solutions, emul-sions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam formers.

If the extender used is water, it is also possible to use, for example, organic solvents as auxiliary solvents. Suitable liquid solvents are essentially: aromatics, such as xylene, toluene or alkylnaph-thalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic colorants, such as alizarin colorants, azo colorants and metal phthalo-cyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), bencarbazone, benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flucetosulfuron, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfurone, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrithiobac (-sodium), pyrimisulfan, quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thiencarbazone-methyl, thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron, triflosulam,

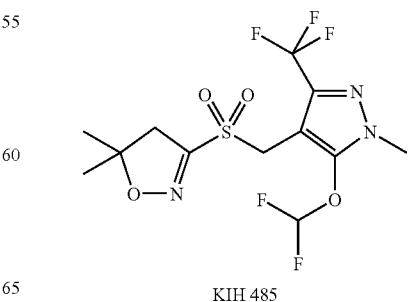

KIH 485

A mixture with other known active compounds, such as fungicides, insecticides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in a customary manner, for example by pouring, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, salts from 0.001 to 1000 parts by weight, preferably from 0.01 to 100 parts by weight, particularly preferably 0.05 to 20 parts by weight, of one of the compounds which improve crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by pouring, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are the important crop plants, such as cereals (wheat, barley, rice), maize, soybeans, potatoes, cotton, oilseed rape, beet, sugar cane and also fruit plants (with the fruits apples, pears, citrus fruits and grapevines), greater emphasis being given to cereals, maize, soybeans, potatoes, cotton and oilseed rape.

The term "active compounds" always also includes the active compound combinations mentioned here.

Preparation and use of the active compounds according to the invention is illustrated by the examples below.

PREPARATION EXAMPLES

Example I-a-1

Process (I)

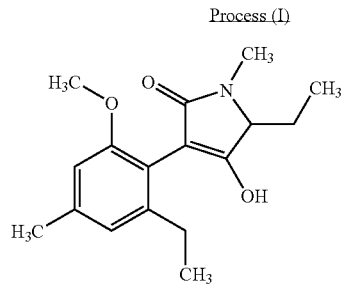

1 g of the compound of Example I-a-6 from WO 05/044791 and 0.085 g of copper(I) bromide and 0.89 ml of methyl acetate are added to 2.77 ml of sodium methoxide solution (30%). The mixture is stirred under reflux for 4 hours. The reaction solution is concentrated to dryness using a rotary evaporator, and the residue is taken up in water. After filtration, the pH is adjusted to 1 using 1 N HCl solution, and the mixture is stirred at room temperature for 10 minutes.

The precipitate is filtered off with suction through a frit.

Yield: 0.6 g (70% of theory). m.p. 85-87° C.

Example I-a-4

Process (A)

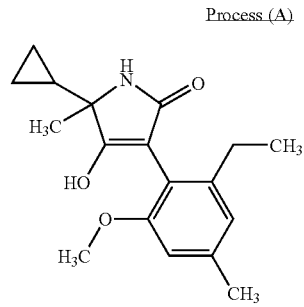

1.63 g of potassium tert-butoxide are initially charged in 20 ml of dimethylformamide (DMF), and 2.2 g of the compound of Example II-1 in 20 ml of DMF are slowly added dropwise. The mixture is stirred at room temperature. After the reaction has ended (monitored by thin-layer chromatography), the solvent is distilled off, the residue is taken up in 200 ml of water and the mixture is adjusted to pH 2 using 1 N HCl. The mixture is extracted with ethyl acetate, the extract is dried over sodium sulfate and the solvent is distilled off.

Yield: 1.71 g (86% of theory), m.p. 180-188° C.

The following compounds of the formula (I-a-1) are obtained analogously to Example (I-a-1) and (I-a-4) and in accordance with the general statements on the preparation:

(I-a)

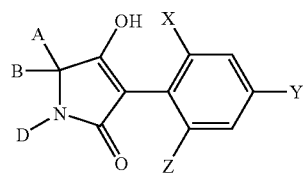

| Ex. No. | X | Y | Z | D | A | B | m.p. °C | Isomer |
|---|---|---|---|---|---|---|---|---|
| I-a-2 | OCH₃ | CH₃ | C₂H₅ |   | —(CH₂)₃— | H | 120-121 | — |
| I-a-3 | OCH₃ | CH₃ | C₂H₅ | H | CH₃ | CH₃ | 147-148 | — |
| I-a-4 | OCH₃ | CH₃ | C₂H₅ | H | △ | CH₃ | 180-182 | — |
| I-a-5 | OCH₃ | CH₃ | C₂H₅ | H | —(CH₂)₂—CHCH₃—(CH₂)₂— | | 229-232 | B |
| I-a-6 | OCH₃ | CH₃ | C₂H₅ | H | —(CH₂)₂—CHOCH₃—(CH₂)₂— | | 112 | B |
| I-a-7 | OCH₃ | CH₃ | C₂H₅ | H | —CH₂—CHOC₄H₉—(CH₂)₃— | | *2.34 (m, 2 H, Ar—CH₂) 3.42 (t, 2 H, O—CH₂) | B |
| I-a-8 | OC₂H₅ | CH₃ | C₂H₅ | H | —(CH₂)₂—CHOCH₃—(CH₂)₂— | | *3.26 (s, 3 H, OCH₃) 3.85 (m, 2 H, Ar—O—CH₂) | β |
| I-a-9 | OCH₃ | CH₃ | C₂H₅ | H | —CH₂—CHOCH₃—(CH₂)₃— | | *3.26 (s, 3 H, OCH₃) 3.66 (s, 3 H, Ar—OCH₃ | B |

¹H-NMR (400 MHz, d₆-DMSO): shift δ in ppm

Example I-b-1

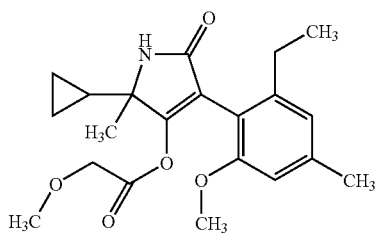

0.18 g of the compound of Example I-a-4 is dissolved in 10 ml of dichloromethane, and 0.09 ml of triethylamine is added. 0.06 ml of methoxyacetyl chloride and 2 ml of dichloromethane is then added, and the mixture is stirred at room temperature overnight. The mixture is added to 10 ml of saturated sodium chloride solution, the organic phase is separated off and the aqueous phase is washed with dichloromethane. The combined organic phases are dried with sodium sulfate, concentrated and purified by column chromatography using n-heptane/ethyl acetate (gradient 1:4 to 0:100).

Yield: 0.22 g (98% of theory) ¹H-NMR (300 MHz, CDCl₃): δ=4.01 (s, 2H, O—CH₂—CO), 1.42 (d, 3H, CH₃) ppm.

The following compounds of the formula (I-b) are obtained analogously to Example (I-b-1) and in accordance with the general statements on the preparation:

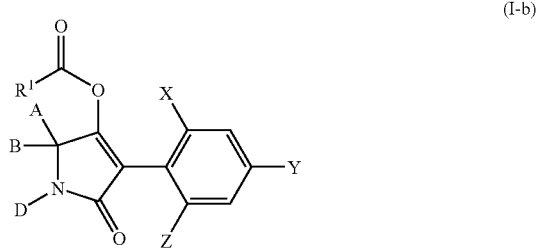

(I-b)

| Ex. No. | X | Y | Z | D | A | B | R¹ | m.p. °C | Isomer |
|---|---|---|---|---|---|---|---|---|---|
| I-b-2 | OCH₃ | CH₃ | C₂H₅ | H | △ | CH₃ | i-C₃H₇ | 125-133 | — |
| I-b-3 | OCH₃ | CH₃ | C₂H₅ | H | CH₃ | CH₃ | i-C₃H₇ | 142 | — |
| I-b-4 | OCH₃ | CH₃ | C₂H₅ | H | —CH₂—CHOC₄H₉—(CH₂)₃— | | i-C₃H₇ | 161-163 | B |
| I-b-5 | OCH₃ | CH₃ | C₂H₅ |   | —CH₂—CHOCH₃—CH₂— | H | H₃C—O—CH₂ | *2.32 (s, 3 H, Ar—CH₃ 4.08 (s, 2 H, O—CH₂—CO) | — |

*¹H-NMR (300 MHz, CDCl₃): shift δ in ppm

Example I-c-1

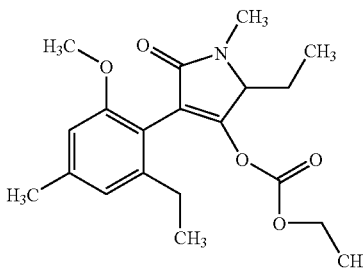

0.2 g of the compound of Example I-a-1 is dissolved in 10 ml of dichloromethane, and 0.11 ml of triethylamine is added. 0.07 ml of ethyl chloroformate is then metered in a little at a time. The mixture is stirred at room temperature for 20 h, and 8 ml of 5% strength sodium carbonate solution are then added. The organic phase is separated off and purified chromatographically on silica gel using ethyl acetate/n-heptane (gradient from 1:4 to 2:1).

Yield: 0.135 g (54% of theory), oil $^1$H-NMR (300 MHz, CDCl$_3$): δ=3.72 (d, 3H, OC$\underline{H}_3$), 4.66 (dq, 2H, N—CH) ppm.

The following compounds of the formula (I-c) are obtained analogously to Example (I-c-1) and in accordance with the general statements on the preparation

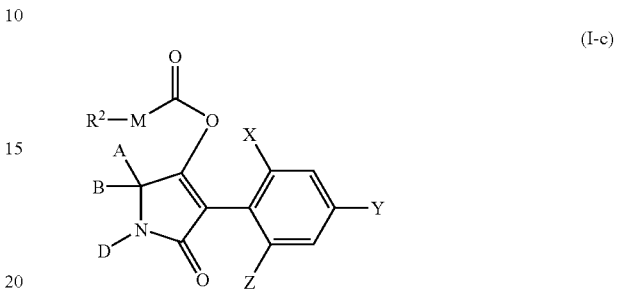

(I-c)

| Ex. No. | X | Y | Z | D | A | B | M | R$^2$ | m.p. °C. | Isomer |
|---|---|---|---|---|---|---|---|---|---|---|
| I-c-2 | OCH$_3$ | CH$_3$ | C$_2$H$_5$ | | —(CH$_2$)$_3$— | H | O | C$_2$H$_5$ | Oil* | — |
| I-c-3 | OCH$_3$ | CH$_3$ | C$_2$H$_5$ | H | CH$_3$ | CH$_3$ | O | C$_2$H$_5$ | *1.42 (d, 6 H, 2 × CH$_3$) 4.02 (q, 2 H, O CH$_3$) | — |
| I-c-4 | OCH$_3$ | CH$_3$ | C$_2$H$_5$ | H | —(CH$_2$)$_2$—CHOCH$_3$—(CH$_2$)$_2$— | | O | C$_2$H$_5$ | 144-148 | β |
| I-c-5 | OCH$_3$ | CH$_3$ | C$_2$H$_5$ | H | ▷ | CH$_3$ | O | C$_2$H$_5$ | *1.51 (d, 3 H, CH$_3$) 4.01 (q, 2 H, O CH$_2$) | — |
| I-c-6 | OCH$_3$ | CH$_3$ | C$_2$H$_5$ | H | —(CH$_2$)$_2$—CHCH$_3$—(CH$_2$)$_2$— | | O | C$_2$H$_5$ | *0.95 (d, 3 H, CH$_3$) 4.02 (q, 2 H, OCH$_2$) | β |
| I-c-7 | OCH$_3$ | CH$_3$ | C$_2$H$_5$ | H | —CH$_2$—CHOC$_4$H$_9$—(CH$_2$)$_3$— | | O | C$_2$H$_5$ | 178-181 | B |
| I-c-8 | OCH$_3$ | CH$_3$ | C$_2$H$_5$ | | —CH$_2$—CHOCH$_3$—CH$_2$— | H | O | C$_2$H$_5$ | *3.36 (s, 3 H, O CH$_3$) 4.19 (q, 2 H, O CH$_2$) | mixture |

*$^1$H-NMR (300 MHz, CDCl$_3$): shift δ in ppm

Example II-1

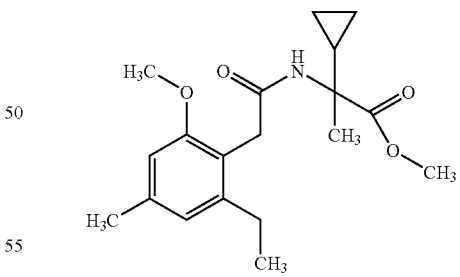

3.88 ml of conc. sulfuric acid are initially charged, and 3.77 g of the compound of Example XXIV-1 in 20 ml of CH$_2$Cl$_2$ are added. The mixture is stirred at 40° C. for 3 h. 20 ml of methanol are added, and the mixture is stirred at 60° C. for 4 h. The mixture is stirred at room temperature overnight. After the reaction is ended, the mixture is added to 200 ml of H$_2$O and extracted with 300 ml of ethyl acetate, and the extract is dried over sodium sulfate and concentrated using a rotary evaporator. The residue is taken up in ethyl acetate and the product is precipitated using n-heptane.

Yield: 2.2 g (53% of theory) ¹H-NMR (300 MHz, CDCl₃): δ=3.53 (s, 2H, Ar—CH₂—CO), 0.26 (m, 2H, cyclopropyl) ppm.

Example II-2

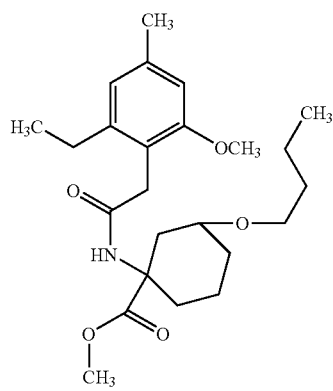

1.52 g of methyl trans-3-butoxy-1-aminocyclohexanecarboxylic hydrochloride and 3.11 g of potassium carbonate are initially charged in 20 ml of dichloromethane. The mixture is stirred at room temperature for 10 min. At T>0° C., 1.5 g of the compound of Example XV-1 in 10 ml of dichloromethane are slowly added dropwise. The mixture is stirred at room temperature until the reaction has ended (monitored by thin-layer chromatography). The reaction mixture is put into 200 ml of water, stirred at room temperature for 10 min and extracted with ethyl acetate, and the organic phase is dried over sodium sulfate and concentrated using a rotary evaporator.

Yield: 1.7 g (65% of theory)

The compound is reacted further without purification. The following compounds of the formula (II) are obtained analogously to Examples (II-1) and (II-2) and in accordance with the general statements on the preparation

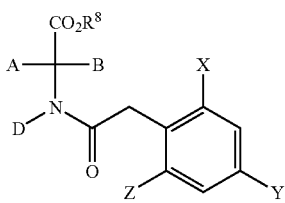

(II)

Example XXIV-1

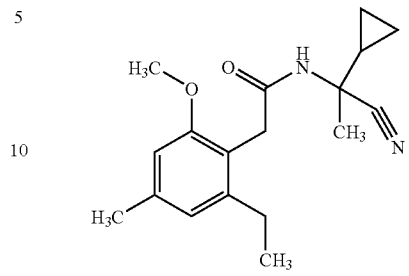

1.46 g of 2-amino-2-cyclopropylpropionitrile and 6.22 g of potassium carbonate are initially charged in 20 ml of CH₂Cl₂ and stirred at room temperature for 10 min. At about 0° C., 3 g of 2-methoxy-6-ethyl-4-methylphenylacetyl chloride (XV-1) in 10 ml of CH₂Cl₂ are slowly added dropwise. The mixture is stirred at room temperature overnight. After the reaction has ended (monitored by thin-layer chromatography), the mixture is added to 200 ml of water, stirred at room temperature for 10 min and extracted with ethyl acetate, and the organic phase is dried over sodium sulfate and concentrated using a rotary evaporator.

Yield: 3.77 g (95% of theory).

The compound is reacted further without purification.

¹H-NMR (300 MHz, CDCl₃): δ=3.59 (s, 2H, Ar—CH₂—CO), 1.71 (s, 3H, NH—C(CH₃)) ppm.

Example XV-1

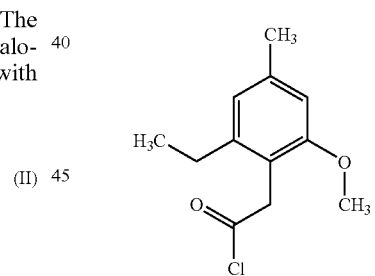

10 g of the compound of Example XVIII-1 are initially charged in 100 ml of dichloromethane. 7.923 g (5.45 ml) of oxalyl chloride are added, and the mixture is stirred under reflux until the evolution of gas has ceased. The solvent is

| Ex. No | X | Y | Z | D | A | B | R⁸ | m.p.° C. | Isomer |
|---|---|---|---|---|---|---|---|---|---|
| II-3 | OCH₃ | CH₃ | C₂H₅ | H | CH₃ | CH₃ | CH₃ | *1.45 (s, 6H, 2 xCH₃)<br>3.57 (s, 2H, Ar—CH₂—CO) | — |
| II-4 | OCH₃ | CH₃ | C₂H₅ | —CH₂—CHOCH₃—CH₂— | | H | CH₃ | *3.34 (s, 2H, Ar—CH₂—CO)<br>3.76 (d, 3H, CO₂CH₃) | mixture |

*¹H-NMR (300 MHz, CDCl₃): shift δ in ppm removed using a rotary evaporator, and the residue is taken up in 50 ml of dichloromethane and then concentrated using a rotary evaporator.

The compound is reacted further without work-up.

Example XVIII-1

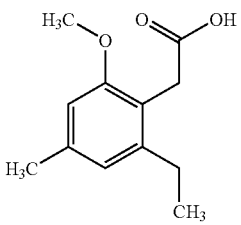

23.49 g of the compound of Example XIX-1 are initially charged in 200 ml of tetrahydrofuran, and 2.784 g of lithium hydroxide and 100 ml of water are added. The mixture is stirred at room temperature overnight and then concentrated using a rotary evaporator. 500 ml of 1N HCl are added to the residue, and the mixture is stirred at room temperature for 10 min and then filtered off with suction through a frit.

Yield: 20 g (91% of theory), m.p: 112° C.

The compound (XVIII-2) is obtained analogously to Example (XVIII-1)

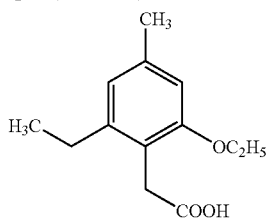

$^1$H-NMR (300 MHz, CDCl$_3$): δ=1.18 (t, 3H, Ar—CH$_2$—$\underline{CH_3}$), 4.01 (q, 2H, Ar—O—$\underline{CH_2}$—CH$_3$) ppm.

Example XIX-1

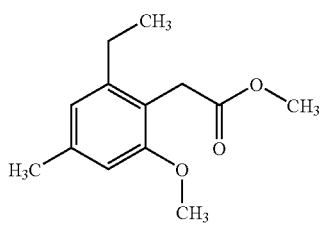

30 g of methyl 2-bromo-4-methyl-6-ethylphenylacetate, known, for example, from WO 05/044796, WO 05/044791 and 103.77 g of sodium methoxide solution (30% strength), 3.174 g of copper(I) bromide and 33.33 ml of methyl acetate are stirred at reflux for 7 h until all of the starting material has reacted. The mixture is concentrated to dryness using a rotary evaporator, the residue is taken up in water and the mixture is filtered off. The aqueous phase is adjusted to pH 1 using HCl and extracted with ethyl acetate, and the organic phase is dried over sodium sulfate and concentrated using a rotary evaporator.

Yield: 23.49 g (96% of theory) $^1$H-NMR (300 MHz, CDCl$_3$): δ=1.18 (t, 3H, CH$_2$—$\underline{CH_3}$) 2.32 (s, 2H, Ar—$\underline{CH_3}$) 2.57 (q, 2H, $\underline{CH_2}$—CH$_3$) 3.65 (4s, 5H, Ar—$\underline{CH_2}$—CO, Ar—OCH$_3$) 3.78 (s, CO—OCH$_3$) 6.55 (s, 1H, Ar—H$_3$) 6.65 (s, 1H, Ar—H$_5$) ppm.

Example A

Myzus Test (spray treatment)

| Solvents: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show good activity:

At an active compound concentration of 500 g/ha, the following compounds achieved a kill rate in % after 5 d of ≧90%: Ex. I-a-5, I-c-4

Example B

Phaedon Test (spray treatment)

| Solvents: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show good activity:

At an active compound concentration of 500 g/ha, the following compounds achieved a kill rate in % after 7 d of ≧80%: Ex. I-a-6, I-c-4

Example C

*Tetranychus* Test (OP Resistance/Spray Treatment)

| Solvents: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of bean leaves (*Phaseolus vulgaris*) which are infested by all stages of the greenhouse red spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show good activity:

At an active compound concentration of 500 g/ha, the following compounds achieved a kill rate in % after 5 d of ≧70%: Ex. I-a-4, I-b-1, I-c-2, I-c-8

At an active compound concentration of 100 g/ha, the following compounds achieved a kill rate in % after 5 d of ≧70%: Ex. I-b-3, I-b-4, I-c-3

Example D

1. Herbicidal Pre-emergence Action

Seeds of monocotyledonous and dicotyledonous weed and crop plants are placed into sandy loam in wood fiber pots and covered with soil. The test compounds, formulated in the form of wettable powders (WP) are then, as an aqueous suspension with a water application rate of 600 l/ha (converted), with 0.2% of wetting agent added, applied to the surface of the covering soil in various dosages.

After the treatment, the pots are placed in the greenhouse and kept under good growth conditions for the test plants. The visual assessment of the emergence damage on the test plants is carried out after a trial period of 3 weeks by comparison with untreated controls (herbicidal effect in percent (%): 100% effect=the plants have died, 0% effect=like control plants).

The following compounds, applied by the pre-emergence method at 320 g of a.i./ha, showed an activity of ≧80% against *Avena sativa, Lolium multiflorum* and *Setaria viridis*: I-a-2, I-a-3, I-a-5, I-a-6, I-c-2, I-c-4

2. Herbicidal Post-emergence Action

Seeds of monocotyledonous and dicotyledonous weed and crop plants are placed into sandy loam in wood fiber pots, covered with soil and cultivated in the greenhouse under good growth conditions. Two to three weeks after sowing, the test plants are treated at the one-leaf stage. The test compounds, formulated as wettable powders (WP), are then, in various dosages with a water application rate of 600 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to untreated controls (herbicidal effect in percent (%): 100% effect=the plants have died, 0% effect=like control plants).

|  | Greenhouse | Dosage (g of a.i./ha) | *Avena* | *Lolium* | *Setaria* |
|---|---|---|---|---|---|
| Ex. I-a-6 | pre-emergence | 320 | 100 | 100 | 100 |

|  | Greenhouse | Dosage (g of a.i./ha) | *Echinochloa* | *Lolium* | *Setaria* |
|---|---|---|---|---|---|
| Ex. I-a-6 | post-emergence | 320 | 100 | 100 | 90 |

-continued

| Ex. I-a-2 | post-emergence | 320 | 100 | 100 | 100 |
|---|---|---|---|---|---|

The following compounds, applied by the post-emergence method at 320 g of a.i./ha, showed an activity of ≧90% against *Avena sativa, Echinocloa crus-galli, Lolium multiflorum* and *Setaria viridis*; I-a-1, I-a-2, I-a-3, I-a-4, I-a-5, I-a-6, I-b-1, I-c-2, I-c-3, I-c-4, I-c-5

Herbicidal Post-emergence Action

Seeds of monocotyledonous and dicotyledonous weed and crop plants are placed into sandy loam in wood fiber pots or in plastic pots, covered with soil and cultivated in a greenhouse, during the vegetation period also outdoors outside of the greenhouse, under good growth conditions. Two to three weeks after sowing, the test plants are treated at the one- to three-leaf stage. The test compounds, formulated as wettable powders (WP) or liquid (EC) are, in various dosages with a water application rate of 300 l/ha (converted), with wetting agent (0.2 to 0.3%) added, sprayed onto the plants and the surface of the soil. Three to four weeks after the treatment of the test plants, the effect of the preparations is rated visually in comparison to untreated controls (herbicidal effect in percent (%):

(100% effect=the plants have died, 0% effect=like control plants).

Use of Safeners

If it is additionally to be tested as to whether safeners can improve the plant compatibility of test substances in the case of crop plants, the following options are used for applying the safener:

seeds of the crop plants are, before sowing, dressed with the safener substance (amount of safener stated in percent, based on the weight of the seed)

before the application of the test substances, the crop plants are sprayed with the safener at a certain application rate per hectare (usually 1 day before the application of the test substances)

the safener is applied together with the test substance as a tank mix (amount of safener stated in g/ha or as a ratio, based on the herbicide).

By comparing the effect of the test substances on crop plants without or with safener treatment, it is possible to assess the effect of the safener substance.

Container Trials with Cereal in a Greenhouse

Mefenpyr 1 Day Prior to Herbicide Application

|  |  | 28 days after application | |
|---|---|---|---|
|  | Application rate g of a.i./ha | Summer barley observed (%) | Summer wheat observed (%) |
| Example I-a-2 | 50 | 90 | 95 |
|  | 25 |  | 60 |
|  | 12.5 |  | 40 |
| Example I-a-2 + Mefenpyr | 50 + 100 | 30 | 30 |
|  | 25 + 100 |  | 20 |
|  | 12.5 + 100 |  | 10 |

Example E

Critical Concentration Test/Soil Insects—Treatment of Transgenic Plants

| | |
|---|---|
| Test insect: | *Diabrotica balteata* - larvae in soil |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that emerged (1 plant=20% effect).

Example F

*Heliothis virescens* Test—Treatment of Transgenic Plants

| | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and populated with the tobacco butworm *Heliothis virescens* while the leaves are still moist.

After the desired period of time, the kill of the insects is determined.

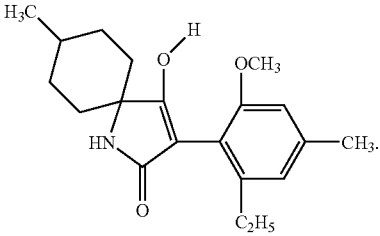

The invention claimed is:

1. A compound of formula (I)

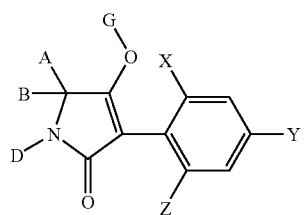

(I)

in which
X represents methoxy,
Y represents methyl,
Z represents ethyl,
A represents hydrogen, in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano-, or nitro-substituted aryl, arylalkyl or heteroaryl,
B represents hydrogen, alkyl or alkoxyalkyl, or
A and B together with the carbon atom to which they are attached represent a saturated or unsaturated $C_4$-$C_8$-ring which optionally contains at least one heteroatom and which is optionally substituted by alkyl, alkoxy or haloalkyl,
D represents hydrogen, $C_1$-$C_8$-alkyl, $C_1$-$C_8$-alkenyl, $C_1$-$C_6$-alkoxy-$C_2$-$C_4$-alkyl or $C_1$-$C_6$-alkylthio-$C_2$-$C_4$-alkyl, each of which is optionally mono- to trisubstituted by halogen; or represents $C_3$-$C_8$-cycloalkyl which is optionally mono- to trisubstituted by halogen, $C_1$-$C_4$-alkyl, $C_1$-$C_4$-alkoxy or $C_1$-$C_2$-haloalkyl, or
A and D together with the atoms to which they are attached represent $C_3$-$C_8$-alkanediyl or $C_3$-$C_6$-alkenediyl in which in each case optionally one methylene group is replaced by oxygen or sulfur and which are in each case optionally mono- or disubstituted by halogen, hydroxyl, $C_1$-$C_4$-alkyl or $C_1$-$C_4$-alkoxy, or by a further $C_3$-$C_6$-alkanediyl, $C_3$-$C_6$-alkenediyl or $C_4$-$C_6$-alkanedienediyl group which forms a fused-on ring,
and
G represents hydrogen (a) or represents one of the groups

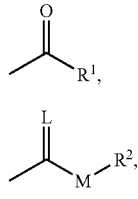

(b)

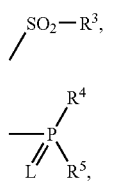

(c)

(d)

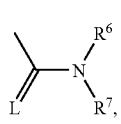

(e)

E  or (f)

(g)

in which
E represents a metal ion or an ammonium ion,
L represents oxygen or sulfur,
M represents oxygen or sulfur,
$R^1$ represents $C_1$-$C_{20}$-alkyl, $C_2$-$C_{20}$-alkenyl, $C_1$-$C_6$-alkoxy-$C_1$-$C_6$-alkyl, $C_1$-$C_6$-alkylthio-$C_1$-$C_6$-alkyl or poly-$C_1$-$C_4$-alkoxy-$C_1$-$C_4$-alkyl, each of which is optionally mono- to heptasubstituted by halogen, mono- or disubstituted by cyano, monosubstituted by $COR^{13}$, $C=N-OR^{13}$, $CO_2R^{13}$, or $$CON\begin{matrix}R^{13}\\R^{13'}\end{matrix};$$

or represents $C_3$-$C_8$-cycloalkyl which is optionally mono- to trisubstituted by halogen, $C_1$-$C_4$-alkyl or $C_1$-$C_4$-alkoxy and in which optionally one or two not directly adjacent methylene groups are replaced by oxygen or sulfur,
  represents phenyl, phenyl-$C_1$-$C_2$-alkyl or phenyl-$C_1$-$C_2$-alkenyl, each of which is optionally mono- to trisubstituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio, $C_1$-$C_6$-alkylsulfinyl or $C_1$-$C_6$-akylsulfonyl,
  represents 5- or 6-membered heteroaryl which is optionally mono- or disubstituted by halogen or $C_1$-$C_6$-alkyl and which has one or two heteroatoms selected from the group consisting of oxygen, sulfur and nitrogen,
$R^2$ represents $C_1$-$C_{20}$-alkyl, $C_2$-$C_{20}$alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by halogen,
  represents $C_3$-$C_8$-cycloalkyl which is optionally mono- or disubstituted by halogen, $C_1$-$C_6$-alkyl or $C_1$-$C_6$-alkoxy or
  represents phenyl or benzyl, each of which is optionally mono- to trisubstituted by halogen, cyano, nitro, $C_1$-$C_6$-alkyl, $C_1$-$C_6$-alkoxy, $C_1$-$C_6$-haloalkyl or $C_1$-$C_6$-haloalkoxy,
$R_3$ represents $C_1$-$C_8$-alkyl which is optionally mono- or polysubstituted by halogen or represents phenyl or benzyl, each of which is optionally mono- or disubstituted by halogen, $C_1$-$C_6$-alkyl, $C_1$-$C_6$-alkoxy, $C_1$-$C_4$-haloalkyl, $C_1$-$C_4$-haloalkoxy, cyano or intro,
$R^4$ and $R^5$ independently of one another represent $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_2$-$C_8$-alkenylthio, each of which is optionally mono- to trisubstitated by halogen; or represent phenyl, phenoxy or phenylthio, each of which is optionally mono- to trisubstituted by halogen, nitro, cyano, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkyl or $C_1$-$C_4$-haloalkyl,
$R^6$ and $R^7$ independently of one another represent hydrogen, $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, each of which is optionally mono- to trisubstituted by halogen; represent phenyl or benzyl, each of which is optionally mono- to trisubstituted by halogen, $C_1$-$C_8$-alkyl, $C_1$-$C_8$-haloalkyl or $C_1$-$C_8$-alkoxy; or together represent a $C_3$-$C_6$-alkylene radical which is optionally mono- or disubstituted by $C_1$-$C_4$-alkyl and in which optionally one methylene group is replaced by oxygen or sulfur,
$R^{13}$ represents $C_1$-$C_6$-alkyl, $C_3$-$C_6$-alkenyl, $C_3$-$C_6$-alkynyl or $C_1$-$C_4$-alkoxy-$C_2$-$C_4$-alkyl, each of which is optionally mono- to trisubstituted by halogen; or represents $C_3$-$C_6$-cycloalkyl which is optionally mono- or disubstituted by halogen, $C_1$-$C_2$-alkyl or $C_1$-$C_2$-alkoxy and in which optionally one or two not directly adjacent methylene groups are replaced by oxygen; or represents phenyl or phenyl-$C_1$-$C_2$-alkyl which are in each case optionally mono- or disubstituted by halogen, $C_1$-$C_4$-alkyl, $C_1$-$C_4$-alkoxy, $C_1$-$C_2$-haloalkyl, $C_1$-$C_2$-haloalkoxy, cyano or nitro, and
$R^{13'}$ represents hydrogen, $C_1$-$C_6$-alkyl or $C_3$-$C_6$-alkenyl.

2. The compound of formula (I) as claimed in claim 1, in which
A represents hydrogen or optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen or sulfur or represents in each case optionally halogen-, $C_1$-$C_6$-alkyl, $C_1$-$C_6$-haloalkyl, $C_1$-$C_6$-alkoxy, $C_1$-$C_6$-haloalkoxy-, cyano- or nitro-substituted phenyl, naphthyl, heteroaryl having 5 to 6 ring atoms, phenyl-$C_1$-$C_6$-alkyl or naphthyl-$C_1$-$C_6$-alkyl,
B represents hydrogen, $C_1$-$C_{12}$-alkyl or $C_1$-$C_8$-alkoxy-$C_1$-$C_6$-alkyl, or
A, B and the carbon atom to which they are attached represent saturated $C_4$-$C_8$-cycloalkyl in which optionally one methylene group is replaced by oxygen or sulfur and which is optionally substituted by $C_1$-$C_6$-alkyl, $C_1$-$C_4$-haloalkyl or $C_1$-$C_6$-alkoxy,
and
D and G are as defined above in claim 1.

3. The compound of formula (I) as claimed in claim 1, in which
A represents hydrogen, $C_1$-$C_6$-alkyl, $C_1$-$C_2$-haloalkyl, $C_1$-$C_4$-alkoxy-$C_1$-$C_3$-alkyl or represents $C_3$-$C_6$-cycloalkyl which is optionally mono- or disubstituted by fluorine, chlorine, $C_1$-$C_2$-alkyl or $C_1$-$C_2$-alkoxy,
B represents hydrogen, $C_1$-$C_2$-alkyl or $C_1$-$C_4$-alkoxy-$C_1$-$C_2$-alkyl,
A, B and the carbon atom to which they are attached represent saturated $C_3$-$C_7$-cycloalkyl in which optionally one methylene group is replaced by oxygen and which is optionally monosubstituted by $C_1$-$C_4$-alkyl, $C_1$-$C_2$-haloalkyl or $C_1$-$C_4$-alkoxy,
D represents hydrogen, $C_1$-$C_6$-alkyl, $C_3$-$C_6$-alkenyl, $C_1$-$C_4$-alkoxy-$C_2$-$C_3$-alkyl or $C_1$-$C_4$-alkylthio-$C_2$-$C_3$-alkyl, each of which is optionally mono- to trisubstituted by fluorine or chlorine, represents $C_3$-$C_6$-cycloalkyl which is optionally mono- or disubstituted by fluorine, chlorine, $C_1$-$C_2$-alkyl, $C_1$-$C_2$-alkoxy or trifluoromethyl, or
A and D together represent a $C_3$-$C_5$-alkanediyl group in which optionally a methylene group is replaced by oxygen or sulfur and which is optionally mono- or disubstituted by $C_1$-$C_2$-alkyl or $C_1$-$C_2$-alkoxy,
or A and D together with the atoms to which they are attached represent one of the groups AD-1 to AD-10 below

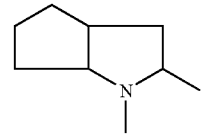

AD-1

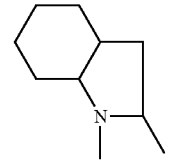

AD-2

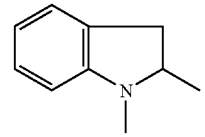

AD-3

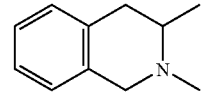

AD-4

-continued

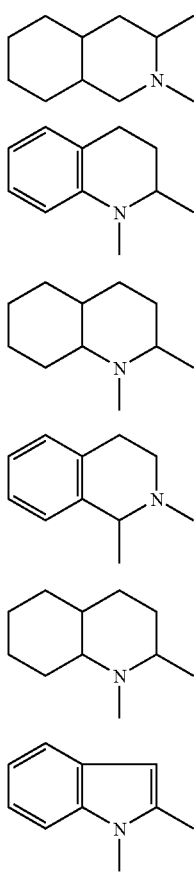

AD-5

AD-6

AD-7

AD-8

AD-9

AD-10

G represents hydrogen (a) or represents one of the groups

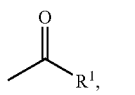 (b)

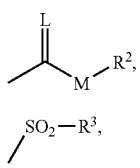 (c)

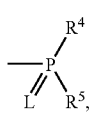 (d)

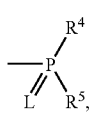 (e)

E or (f)

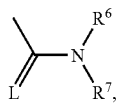 (g)

in which
E represents a metal ion or an ammonium ion,
L represents oxygen or sulfur and
M represents oxygen or sulfur,
$R_1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl or poly-$C_1$-$C_3$-alkoxy-$C_1$-$C_2$-alkyl, each of which is optionally mono- to pentasubstituted by fluorine or chlorine, monosubstituted by cyano, monosubstituted by CO—$R^{13}$, C=N—$OR^{13}$ or $CO_2R^{13}$, represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent methylene groups are replaced by oxygen, represents phenyl or benzyl, each of which is optionally mono- or disubstituted by fluorine, chlorine, bromine, cyano, nitro, $C_1$-$C_4$-alkyl, $C_1$-$C_4$-alkylthio, $C_1$-$C_4$-alkylsulfinyl, $C_1$-$C_4$-alkylsulfonyl, $C_1$-$C_4$-alkoxy, $C_1$-$C_2$-haloalkyl or $C_1$-$C_2$-haloalkoxy, or represents pyrazolyl, thiazolyl, pyridyl, pyrimidyl, furanyl or thienyl, each of which is optionally mono- or disubstituted by fluorine, chlorine, bromine or $C_1$-$C_2$-alkyl, $R^2$ represents $C_1$-$C_{10}$-alkyl, $C_2$-$C_{10\text{-}alkenyl}$, $C_1$-$C_4$-alkoxy-$C_2$-$C_4$-alkyl or poly-$C_1$-$C_4$-alkoxy-$C_2$-$C_4$-alkyl, each of which is optionally mono- to trisubstituted by fluorine or chlorine, represents $C_3$-$C_7$-cycloalkyl which is optionally monosubstituted by fluorine, chlorine, $C_1$-$C_2$-alkyl or $C_1$-$C_2$-alkoxy or represents phenyl or benzyl, each of which is optionally mono- or disubstituted by fluorine, chlorine, bromine, cyano, nitro, $C_1$-$C_4$-alkyl, methoxy, trifluoromethyl or trifluoromethoxy, $R^3$ represents $C_1$-$C_4$-alkyl which is optionally mono- to trisubstituted by fluorine or chlorine or represents phenyl or benzyl, each of which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R_4$ and $R_5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, trifluoromethoxy, $C_1$-$C_3$-alkylthio, $C_1$-$C_3$-alkyl or trifluoromethyl, $R^6$ and $R^7$ independently of one another represent hydrogen, represent $C_1$-$C_6$-alkyl, $C_3$-$C_6$-cycloalkyl, $C_1$-$C_4$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl which is optionally mono- or disubstituted by fluorine, chlorine, bromine, trifluoromethyl, $C_1$-$C_4$-alkyl or $C_1$-$C_4$-alkoxy, or together represent a $C_5$-$C_6$-alkylene radical which is optionally mono- or disubstituted by methyl and in which optionally one methylene group is replaced by oxygen, $R^{13}$ represents $C_1$-$C_4$-alkyl, $C_3$-$C_4$-alkenyl, $C_3$-$C_4$-alkynyl or $C_1$-$C_4$-alkoxy- $C_2$-$C_3$-alkyl or $C_3$-$C_4$-cycloalkyl in which optionally one methylene group is replaced by oxygen, with the proviso that when A represents hydrogen or $C_1$-$C_3$-alkyl, D is not hydrogen.

4. The compound of formula (I) as claimed in claim 1, in which

A represents hydrogen, methyl, ethyl, n-propyl, isopropyl, n-butyl, isobutyl, sec-butyl, tert-butyl, trifluoromethyl, cyclopropyl, cyclopentyl or cyclohexyl, B represents hydrogen, methyl or ethyl, or A, B and the carbon atom to which they are attached represent saturated $C_6$-cycloalkyl in which optionally one methylene group is replaced by oxygen and which is optionally monosubstituted by methyl, trifluoromethyl, methoxy, ethoxy, n-propoxy, isopropoxy, n-butoxy or isobutoxy, D represents hydrogen, methyl, ethyl, n-propyl, isopropyl, n-butyl, sec- butyl, isobutyl, cyclopropyl, cyclopentyl or cyclohexyl, or A and D together represent a $C_3$-$C_4$-alkanediyl group in which in each case optionally one methylene group is replaced by oxygen or sulfur and which is optionally mono- or disubstituted by methyl or methoxy or A and D together with the atoms to which they are attached represent the following group:

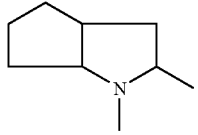

AD-1

G represents hydrogen (a) or represents one of the groups

(b)

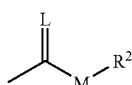

(c)

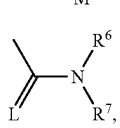

(g)

in which
L represents oxygen and
M represents oxygen or sulfur,
$R^1$ represents $C_1$-$C_6$-alkyl, $C_2$-$C_6$-alkenyl, $C_1$-$C_2$-alkoxy-$C_1$-$C_2$-alkyl, $C_1$-$C_2$-alkylthio-$C_1$-$C_2$-alkyl or poly-$C_1$-$C_2$-alkoxy-$C_1$-$C_2$-alkyl, each of which is optionally mono- to trisubstituted by fluorine or chlorine, or represents cyclopropyl, cyclopentyl or cyclohexyl, each of which is optionally monosubstituted by fluorine, chlorine, methyl, ethyl or methoxy, represents phenyl which is optionally monosubstituted by fluorine, chlorine, bromine, cyano, nitro, methyl, ethyl, n-propyl, isopropyl, methoxy, ethoxy, methylthio, ethylthio, methylsulfinyl, ethylsulfinyl, methylsulfonyl, ethylsulfonyl, trifluoromethyl or trifluoromethoxy, or represents furanyl, thienyl or pyridyl, each of which is optionally monosubstituted by chlorine, bromine or methyl, $R^2$ represents $C_1$-$C_8$-alkyl, $C_2$-$C_6$-alkenyl or $C_1$-$C_3$-alkoxy-$C_2$-$C_3$-alkyl, cyclopentyl or cyclohexyl, or represents phenyl or benzyl, each of which is optionally monosubstituted by fluorine, chlorine, bromine, cyano, nitro, methyl, methoxy, trifluoromethyl or trifluoromethoxy, $R^6$ represents hydrogen, represents $C_1$-$C_4$-alkyl, $C_3$-$C_6$-cycloalkyl or allyl, represents phenyl which is optionally monosubstituted by fluorine, chlorine, bromine, methyl, methoxy or trifluoromethyl, $R^7$ represents methyl, ethyl, n-propyl, isopropyl or allyl, $R^6$ and $R^7$ together represent a $C_5$-$C_6$-alkylene radical in which optionally one methylene group is replaced by oxygen;

with the proviso that when A represents hydrogen, methyl or ethyl, D is not hydrogen.

5. The compound of formula (I) as claimed in claim 1, in which

A represents methyl, ethyl or cyclopropyl,

B represents hydrogen or methyl, or

A, B and the carbon atom to which they are attached represent cyclohexyl which is optionally monosubstituted by methyl, ethoxy or n-butoxy, D represents hydrogen or methyl or A and D together represent a $C_3$-$C_4$-alkanediyl group which is optionally monosubstituted by methoxy, G represents hydrogen (a) or represents one of the groups

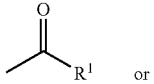

(b)

or

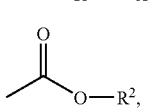

(c)

in which
$R^1$ represents $C_1$-$C_6$-alkyl or $C_1$-$C_2$-alkoxy-$C_1$-$C_2$-alkyl,
$R^2$ represents $C_1$-$C_8$-alkyl;
with the proviso that when A represents ethyl, D represents methyl.

6. A process for preparing a compound of formula (I) as claimed in claim 1, comprising
(A) obtaining a compound of formula (I-a), (I-a)

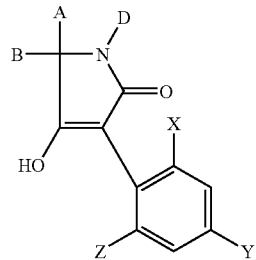

in which
A, B, D, X, Y and Z are as defined in claim 1, by intramolecular condensation of
a compound of formula (II), (II)

in which
A, B, D, X, Y and Z are as defined above,
and
$R^8$ represents alkyl
in the presence of a diluent and in the presence of a base, (B) obtaining a compound of formula (I-b)

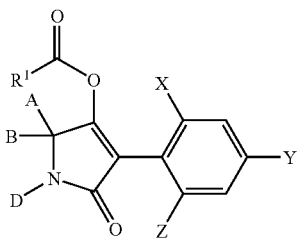
(I-b)

in which A, B, D, X, Y and Z are as defined above, and
$R^1$ represents in each case optionally substituted alkyl, alkenyl, alkoxyalkyl, alkylthioalkyl or polyalkoxyalkyl or represents in each case optionally halogen-, alkyl-, or alkoxy-substituted cycloalkyl or heterocyclyl or represents in each case optionally substituted phenyl, phenylalkyl, phenylalkenyl or heteroaryl, by reacting a compound of formula (I-a) shown above in which A, B, D, X, Y and Z are as defined above α) with an acid halide of formula (III),

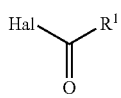
(III)

in which
$R^1$ is as defined above and
Hal represents halogen
or

β) with a carboxylic anhydride of formula (IV), $R^1$—CO—O—CO—$R^1$ (IV)

in which
$R^1$ is as defined above,
optionally in the presence of a diluent and optionally in the presence of an acid binder, (C) obtaining a compound of formula (I-c)

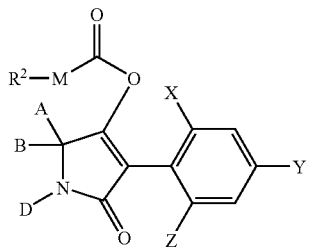
(I-c)

in which A, B, D, X, Y and Z are as defined above and
$R^2$ represents in each case optionally halogen-substituted alkyl, alkenyl, alkoxyalkyl or polyalkoxyalkyl or represents in each case optionally substituted cycloalkyl, phenyl or benzyl,
M represents oxygen or sulfur,
by reacting a compound of formula (I-a) shown above in which A, B, D, X, Y and Z are as defined above with a chloroformic ester or chloroformic thioester of formula (V), $R^2$-M-CO—Cl (V)

in which
$R^2$ and M are as defined above,
optionally in the presence of a diluent and optionally in the presence of an acid binder, (D) obtaining a compound of formula (I-c) shown above in which A, B, D, $R^2$, M, X, Y and Z are as defined above, by reacting a compound of formula (I-a) shown above in which A, B, D, X, Y and Z are as defined above α) with a chloromonothioformic ester or chlorodithioformic ester of formula (VI),

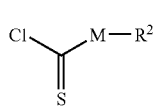
(VI)

in which
M and $R^2$ are as defined above,
optionally in the presence of a diluent and optionally in the presence of an acid binder, or β) with carbon disulfide and then with a compound of formula (VII), $R^2$-Hal (VII)

in which
$R^2$ is as defined above and
Hal represents chlorine, bromine or iodine, optionally in the presence of a diluent and optionally in the presence of a base, (E) obtaining a compound of formula (I-d)

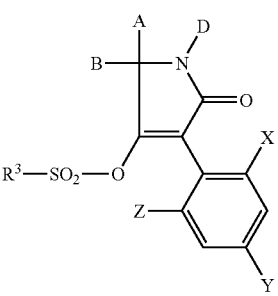
(I-d)

in which A, B, D, X, Y and Z are as defined above,
$R_3$ represents optionally halogen-substituted alkyl, alkoxy, alkylamino, dialkylamino, alkylthio, alkenylthio or cycloalkylthio or represent in each case optionally substituted phenyl, benzyl, phenoxy or phenylthio,
by reacting a compound of formula (I-a) shown above in which A, B, D, X, Y and Z are as defined above with a sulfonyl chloride of formula (VIII), $R^3$—$SO_2$—Cl (VIII)

in which
$R^3$ is as defined above,
optionally in the presence of a diluent and optionally in the presence of an acid binder, (F) obtaining a compound of formula (I-e)

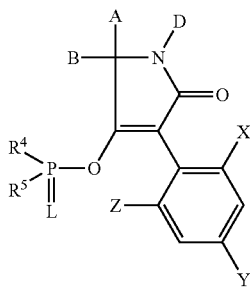
(I-e)

in which A, B, D, L, X, Y and Z are as defined above,
$R_4$ and $R_5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, and
L represents oxygen,
by reacting a compound of formula (I-a) shown above in which A, B, D, X, Y and Z are as defined above with a phosphorus compound of formula (IX),

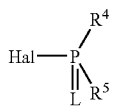
(IX)

in which
L, $R_4$ and $R_5$ are as defined above and
Hal represents halogen,
optionally in the presence of a diluent and optionally in the presence of an acid binder, (G) obtaining a compound of formula (I-f)

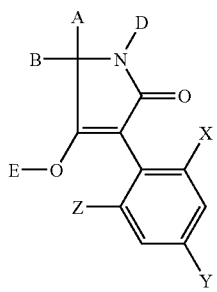
(I-f)

in which A, B, D, X, Y and Z are as defined above, and
E represents a metal ion equivalent or an ammonium ion,
by reacting a compound of formula (I-a) shown above in which A, B, X, Y and Z are as defined above with a metal compound or amine of formula (X) or (XI),

(X)

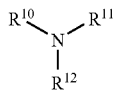
(XI)

in which
Me represents a mono- or divalent metal,
t represents the number 1 or 2, and $R^{10}$, $R^{11}$, $R^{12}$ independently of one another represent hydrogen or alkyl, optionally in the presence of a diluent, (H) obtaining a compound of formula (I-g) shown above

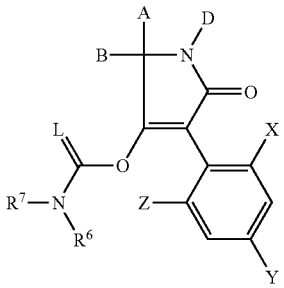
(I-g)

in which A, B, D, L, X, Y and Z are as defined above,
$R^6$ and $R^7$ independently of one another represent hydrogen, in each case optionally halogen-substituted alkyl, cycloalkyl, alkenyl, alkoxy, alkoxyalkyl, optionally substituted phenyl or beuzyl, or together with the N-atom to which they are attached form an optionally substituted cycle which optionally contains oxygen or sulfur;
by reacting a compound of formula (I-a) shown above in which A, B, D, X, Y and Z are as defined above
α) with an isocyanate or isothiocyanate of formula (XII), $$R^6{-}N{=}C{=}L \qquad (XII)$$

in which
$R^6$ and L are as defined above,
optionally in the presence of a diluent and optionally in the presence of a catalyst, or
β) with a carbamoyl chloride or a thiocarbamoyl chloride of formula (XIII),

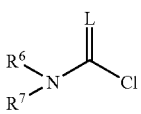
(XIII)

in which
L, $R^6$ and $R^7$ are as defined above,
optionally in the presence of a diluent and optionally in the presence of an acid binder, or (I) obtaining a compound of formula (I-a) shown above in which A, B, D, X, Y and Z are as defined above, by reacting a compound of formula (I-a')

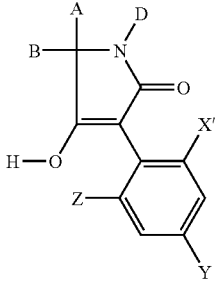
(I-a')

in which
A, B, D, Y and Z are as defined above, and
X' represents chlorine, bromine, iodine
with an alcohol of formula (XXV)

(XXV)

in which
X is as defined above and
in the presence of a solvent, a base and a catalyst.

7. A composition comprising an effective amount of an active compound combination comprising,
(a') at least one compound according to claim 1, and
(b') at least one crop plant tolerance promoter compound selected from the group consisting of:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy) acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N -(1,3-dioxolan-2-ylmethyl)-N-(2-propenyl)acetamide (PPG-1292), 3-dichloroacetyl-2, 2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3 -carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415),4-chlorophenoxyacetic acid, 3,3'-dimethyl-4-methoxybenzophenone, 1-bromo-4-chloromethylsulfonylbenzene, 1-[4-(N-2-methoxybenzoylsulfamoyl)phenyl]-3-methylurea (also known as N-(2-methoxybenzoyl)-4-[(methylaminocarbonyl)amino]benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, and N-(2-methoxy-5-methylbenzoyl)-4-(cyclopropylaminocarbonyl)benzenesulfonamide, or one of the following compounds, defined by formula (IIa)

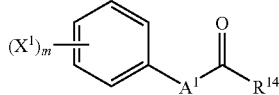

(IIa)

or general formula (IIb)

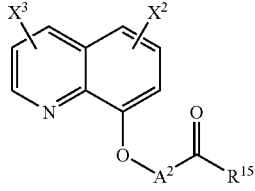

(IIb)

or formula (IIc)

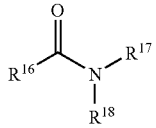

(IIc)

where
m represents a number 0, 1, 2, 3,4 or 5,
$A^1$ represents one of the divalent heterocyclic groupings shown below

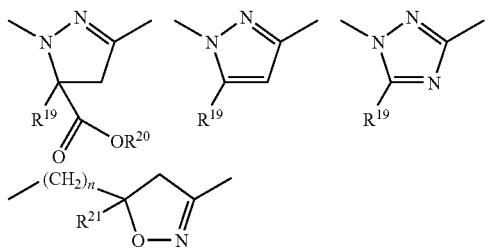

n represents a number 1, 2, 3, 4 or 5,
$A^2$ represents optionally $C_1$-$C_4$-alkyl-, $C_1$-$C_4$-alkoxy-carbonyl- or alkenyloxy-carbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)-amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di-($C_1$-$C_4$-alkyl)-amino, $R^{16}$ represents in each case optionally fluorine-, chlorine- or bromine- substituted $C_1$-$C_4$-alkyl, $R^{17}$ represents hydrogen, in each case optionally fluorine-, chlorine- or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$- alkyl, dioxolanyl-$C_1$-$C_4$-alkyl, furyl, furyl-$C_1$-$C_4$-alkyl, thienyl, thiazolyl, piperidinyl, or optionally fluorine-, chlorine- or bromine- or $C_1$-$C_4$-alkyl-substituted phenyl, $R^{18}$ represents in each case optionally fluorine-, chlorine- or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$- alkyl, dioxolanyl-$C_1$-$C_4$-alkyl, furyl, furyl-$C_1$-$C_4$-alkyl, thienyl, thiazolyl, piperidinyl, or optionally fluorine-, chlorine- or bromine- or $C_1$-$C_4$-alkyl-substituted phenyl, or $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- or bromine-substituted $C_1$-$C_4$-alkyl, $C_3$-$C_6$-cycloalkyl or phenyl, $R^{20}$ represents hydrogen, or in each case optionally hydroxyl-, cyano-, halogen- or $C_1$-$C_4$-alkoxy-substituted $C_1$-$C_6$-alkyl, $C_3$-$C_6$-cycloalkyl or tri-( $C_1$-$C_4$-alkyl)- silyl, $R^{21}$ represents hydrogen, cyano, halogen, or in each case optionally fluorine-, chlorine- or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$- alkoxy or $C_1$-$C_4$-haloalkoxy, $X^2$ represents hydrogen, cyano, halogen, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, or a compound of formula (IId)

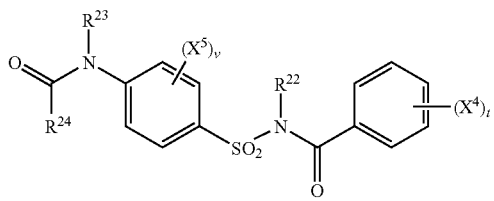

(IId)

or of formula (IIe)

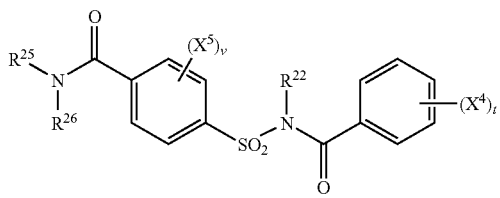

(IIe)

where
t represents a number between 0 and 5,
v represents a number between 0 and 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di- ($C_1$-$C_4$-alkyl)-amino, or in each case optionally cyano-, halogen- or $C_1$-$C_4$-alkyl- substituted $C_3$-$C_6$-cycloalkyl, $C_3$-$C_6$-cycloalkyloxy, $C_3$-$C_6$-cycloalkylthio or $C_3$-$C_6$- cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl- substituted $C_3$-$C_6$-cycloalkyl, $R_{26}$ represents hydrogen, optionally cyano-, hydroxyl-, halogen- or $C_1$-$C_4$- alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$- haloalkoxy, or combinations thereof.

8. The composition as claimed in claim 7 in which the crop plant tolerance promoter compound is selected from the group consisting of:
cloquintocet-mexyl, fenchlorazole-ethyl, isoxadifen-ethyl, mefenpyr-diethyl, fririlazole, fenclorim, cumyluron, dymron and the compounds IIe-5 or IIe-11.

9. The composition as claimed in claim 7 in which the crop plant tolerance promoter compound is mefenpyr-diethyl.

10. A pesticide or herbicide composition comprising at least one compound as claimed in claim 1.

11. A method for controlling animal pests or unwanted vegetation, comprising contacting pests or their habitat with a compound as claimed in claim 1.

12. A process for preparing pesticides or herbicides, comprising mixing a compound of formula (I) according to claim 1 with extenders or surfactants.

13. A method for controlling unwanted vegetation, comprising contacting plants or their habitat with a composition as claimed in claim 7.

14. A method for controlling unwanted vegetation, comprising contacting plants or their habitat with a compound as claimed in claim 1 and a crop plant tolerance promoter compound according to claim 7 separately in temporal succession, or as a mixture.

15. A compound of the following formula: